US010527638B2

(12) United States Patent
Mizuki

(10) Patent No.: US 10,527,638 B2
(45) Date of Patent: Jan. 7, 2020

(54) AUTOMATED ANALYZER AND NOZZLE-CLEANING METHOD

(71) Applicants: JEOL Ltd., Tokyo (JP); Fujirebio Inc., Tokyo (JP)

(72) Inventor: Nakamura Mizuki, Tokyo (JP)

(73) Assignees: JEOL Ltd., Tokyo (JP); Fujirebio Inc., Tokyo (JP)

(*) Notice: Subject to any disclaimer, the term of this patent is extended or adjusted under 35 U.S.C. 154(b) by 379 days.

(21) Appl. No.: 15/310,300

(22) PCT Filed: May 7, 2015

(86) PCT No.: PCT/JP2015/063235
§ 371 (c)(1),
(2) Date: Nov. 10, 2016

(87) PCT Pub. No.: WO2015/174325
PCT Pub. Date: Nov. 19, 2015

(65) Prior Publication Data
US 2017/0153263 A1    Jun. 1, 2017

(30) Foreign Application Priority Data

May 13, 2014 (JP) .................... 2014-099230

(51) Int. Cl.
*B01L 3/00* (2006.01)
*G01N 35/10* (2006.01)
(Continued)

(52) U.S. Cl.
CPC ............ *G01N 35/10* (2013.01); *B08B 3/04* (2013.01); *B08B 9/023* (2013.01); *B08B 9/035* (2013.01);
(Continued)

(58) Field of Classification Search
CPC ....... B01L 3/02; B01L 3/0275; B01L 2200/14
(Continued)

(56) References Cited

U.S. PATENT DOCUMENTS

2010/0047128 A1   2/2010   Mototsu et al.
2010/0098590 A1   4/2010   Inamura et al.
(Continued)

FOREIGN PATENT DOCUMENTS

EP    2184610 A1   5/2010
EP    2390669 A2   11/2011
(Continued)

*Primary Examiner* — Natalia Levkovich
(74) *Attorney, Agent, or Firm* — The Webb Law Firm

(57) ABSTRACT

To clean a nozzle that is part of an automated analyzer and is provided with both a tubular discharge unit that discharges a cleaning liquid and a tubular suction unit that suctions in cleaning liquid that was discharged from the discharge unit and is running down an outer surface, first the discharge unit is made to start discharging, and then in parallel with said discharging, the suction unit is made to start suctioning. After the suction unit has suctioned in the cleaning liquid running down the aforementioned outer surface for a prescribed length of time, the suctioning is temporarily stopped. Next, after a prescribed amount of the cleaning liquid has accumulated in a cleaning tank, the discharging is stopped, and with the suction unit immersed in the cleaning liquid accumulated in the cleaning tank, the suctioning is restarted.

7 Claims, 13 Drawing Sheets

(51) Int. Cl.
*B08B 3/04* (2006.01)
*B08B 9/023* (2006.01)
*B08B 9/035* (2006.01)
*B08B 9/02* (2006.01)

(52) U.S. Cl.
CPC ............ *G01N 35/1004* (2013.01); *B08B 9/02* (2013.01); *B08B 2209/032* (2013.01)

(58) Field of Classification Search
USPC .................................................. 422/501, 500
See application file for complete search history.

(56) References Cited

U.S. PATENT DOCUMENTS

2010/0254857 A1\* 10/2010 Mazume .............. G01N 35/025
 422/82.05
2010/0284862 A1 11/2010 Kakizaki et al.
2011/0293474 A1 12/2011 Sugimura et al.

FOREIGN PATENT DOCUMENTS

| | | |
|---|---|---|
| JP | 5523417 A | 2/1980 |
| JP | 2005283246 A | 10/2005 |
| JP | 200793521 A | 4/2007 |
| JP | 2009174876 A | 8/2009 |
| JP | 2010133924 A | 6/2010 |
| WO | 9703766 A1 | 2/1997 |

\* cited by examiner

AUTOMATED ANALYZER AND NOZZLE-CLEANING METHOD

CROSS-REFERENCE TO RELATED APPLICATIONS

This application is the United States national phase of International Application No. PCT/JP2015/063235, filed May 7, 2015, which claims priority to Japanese Patent Application No. 2014-099230, filed May 13, 2014, the disclosures of which are hereby incorporated herein in their entirety by reference.

TECHNICAL FIELD

The present invention relates to an automated analyzer and a nozzle-cleaning method, and, more particularly, to a technology of cleaning a nozzle that discharges and sucks a liquid, such as a sample liquid or a reagent liquid.

BACKGROUND ART

An automated analyzer is used in tests in various fields, such as in immunological tests, biochemical tests, and blood transfusion tests; performs analytical processing on multiple samples at the same time; and analyzes multiple components quickly with high precision.

Hitherto, an automated analyzer has included a nozzle cleaning mechanism for cleaning a probe in order to prevent a carry-over that influences analysis results from occurring when a liquid, such as a sample liquid or a reagent liquid, that has been dispensed first is carried over to a liquid that is subsequently dispensed while the liquid that has been dispensed first remains adhered to the probe. Such a nozzle cleaning mechanism is formed so as to supply a cleaning liquid to the probe. In a nozzle-cleaning method using the nozzle cleaning mechanism, after sucking and discharging the liquid and completing the dispensing, the probe is moved to the position of the nozzle cleaning mechanism, and the cleaning liquid is supplied to the probe to clean the probe.

For example, PTL 1 describes a nozzle cleaning technology in which a nozzle including a discharge nozzle and a suction nozzle is used to perform a cleaning operation including discharge and suction of a cleaning liquid at least two times. This nozzle is formed such that a lower end of the discharge nozzle is disposed above a lower end of the suction nozzle by a prescribed length.

In the technology described in PTL 1, when cleaning the nozzle, first, the nozzle is inserted into a cleaning tank such that a front end of the suction nozzle is positioned near a bottom portion of the cleaning tank. Next, a first liquid amount of cleaning liquid (first cleaning liquid) is injected into the cleaning tank by the discharge nozzle, and the first cleaning liquid is sucked by the suction nozzle. Then, a second liquid amount of cleaning liquid (second cleaning liquid) that exceeds the first liquid amount is injected into the cleaning tank by the discharge nozzle and the second cleaning liquid is sucked by the suction nozzle.

In this way, in the technology described in PTL 1, the cleaning liquid amount that is discharged during the cleaning is divided in at least two amounts, that is, the first cleaning liquid amount and the second cleaning liquid amount; and is discharged. The first cleaning liquid amount is an amount that allows the nozzle to be immersed up to a height at which a front end portion of the suction nozzle is immersed in a liquid, such as a reagent liquid or a sample liquid, when the nozzle is immersed in the liquid; and the second cleaning liquid amount is an amount at which the cleaning tank is approximately full. That is, in the technology described in PTL 1, a high-concentration contaminated region up to the aforementioned height from a lower end of the suction nozzle is cleaned by using the first cleaning liquid, and a low-concentration contaminated region up to a prescribed height from the lower end of the suction nozzle is cleaned by using the second cleaning liquid.

CITATION LIST

Patent Literature

PTL 1: Japanese Unexamined Patent Application Publication No. 2005-283246

SUMMARY OF INVENTION

Technical Problem

In recent years, automated analyzers are required to provide high analysis precision. Therefore, in order to suppress a carry-over of a liquid, such as a reagent liquid or a sample liquid, there is a demand for increasing cleaning performance of a nozzle with which a liquid contacts directly.

In particular, immunological tests whose analysis performance is required to have higher precision than that for biochemical analyses include a so-called BF separation operation in which components that have specifically combined with immune adsorbates and components that have not combined in a reaction process when a sample is analyzed are separated. In order to perform immunity measurements with high sensitivity, the BF separation is required to separate the immune adsorbate including, for example, magnetic particles with high performance. However, in the BF separation, when the nozzle with which a liquid, such as a reagent liquid or a sample liquid, contacts is not sufficiently cleaned, the immune adsorbates are separated with lower separation performance, as a result of which the immunity measurements are performed with lower sensitivity.

In the technology described in PTL 1, after injecting the first cleaning liquid into the cleaning tank, the first cleaning liquid is sucked, and the second cleaning liquid is subsequently injected into the cleaning tank. That is, a liquid (contaminant) adhered to the front end portion of the suction nozzle is mixed with the first cleaning liquid, and the second cleaning liquid is injected to a portion immersed in the first cleaning liquid in the cleaning tank. Therefore, the second cleaning liquid that is injected into the cleaning tank afterwards is contaminated by the first cleaning liquid with which the liquid adhered to the suction nozzle is mixed.

The present invention is made in consideration of such circumstances. It is an object of the present invention to provide a higher cleaning effect than before in cleaning a nozzle including a discharge nozzle and a suction nozzle.

Solution to Problem

To this end, according to an embodiment of the present invention, when cleaning a nozzle that is part of an automated analyzer and that includes a tubular discharge unit that discharges a cleaning liquid and a tubular suction unit that sucks the cleaning liquid discharged from the discharge unit and running down an outer peripheral surface, first, a discharge operation performed by the discharge unit is started and a suction operation performed by the suction unit is started in parallel with the discharge operation performed by the discharge unit. Then, after the suction unit sucks the cleaning liquid running down the outer peripheral surface for a prescribed length of time, the suction operation performed by the suction unit temporarily ends. Next, after a prescribed amount of the cleaning liquid has accumulated in a cleaning tank, the discharge operation performed by the discharge unit ends. Then, the suction operation performed by the suction unit is restarted with the suction unit immersed in the cleaning liquid accumulated in the cleaning tank.

Advantageous Effects of Invention

According to at least one embodiment of the present invention, when the cleaning liquid that is discharged from the discharge unit runs down the outer peripheral surface of the suction unit and is sucked by the suction unit, the time of contact of a lower end portion of the suction part with the cleaning liquid can be made relatively longer than the time of contact of other portions thereof with the cleaning liquid. Since the cleaning liquid discharged from the discharge unit does not accumulate in the cleaning tank before the suction unit temporarily ends its suction operation, the cleaning liquid in which the suction unit is immersed is not contaminated by cleaning water discharged before the suction operation is temporarily ended. Therefore, a higher cleaning effect is provided than before.

DESCRIPTION OF EMBODIMENTS

Figure 1:
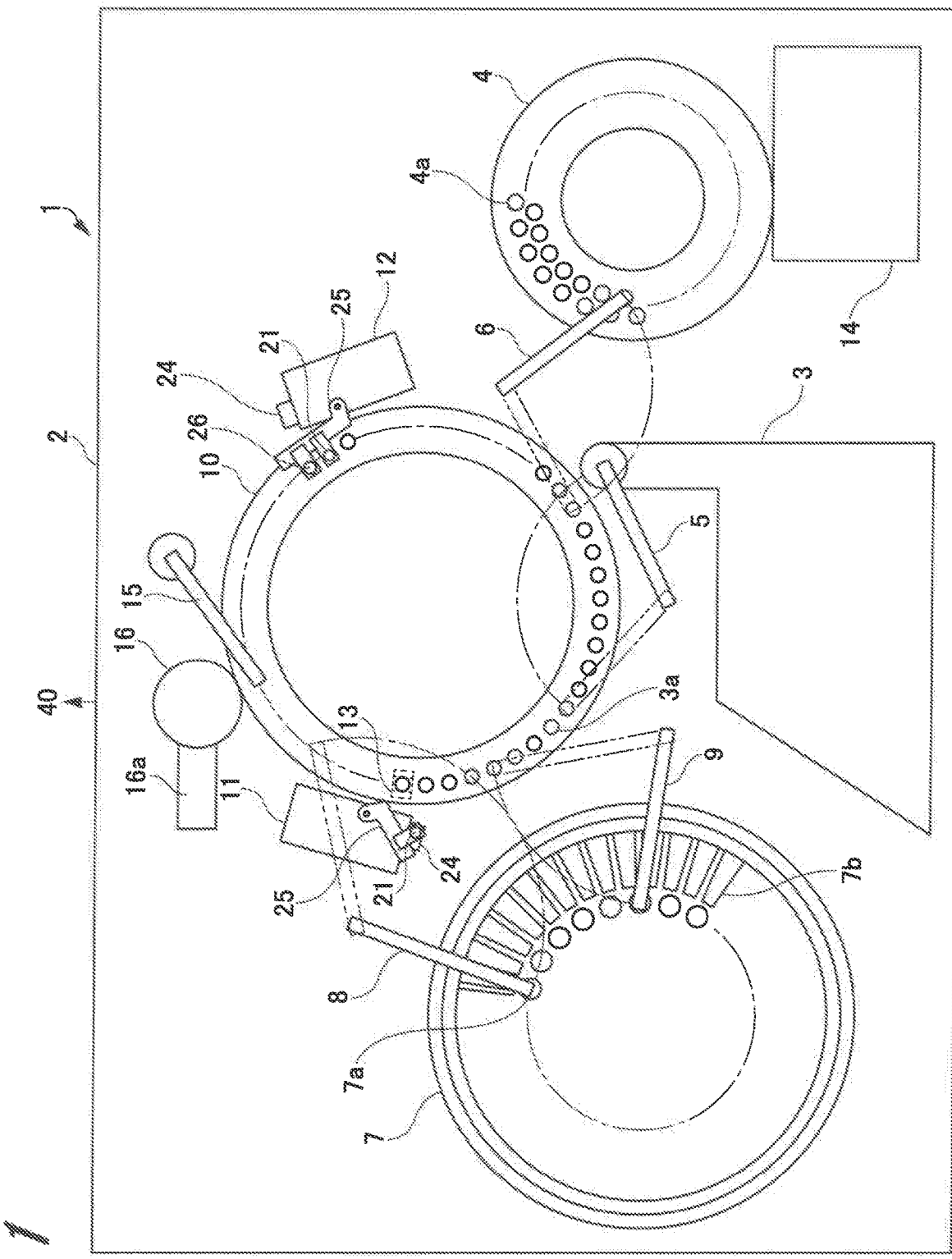
FIG. 1 is a schematic structural view of an automated analyzer according to a first embodiment of the present invention.

Embodiments for carrying out the present invention are described below with reference to the attached drawings. In the figures, common component parts are given the same reference numeral, and the same descriptions thereof are not repeated.

1. First Embodiment

[General Description of Automated Analyzer]

FIG. 1 is a schematic structural view of an automated analyzer according to a first embodiment of the present invention.

The automated analyzer 1 shown in FIG. 1 is applied to an immunology analyzer that performs immunology analysis of, for example, an antigen-antibody reaction of a sample. The automated analyzer 1 includes a measuring device 2 and a controlling device 40 that controls the entire automated analyzer 1 including the measuring device 2 and that analyzes measurement data that is output from the measuring device 2.

The automated analyzer 1 that is applied to an immunology analyzer performs measurements with high sensitivity by using, for example, Chemiluminescent Enzyme Immunoassay (CLEIA). The main steps of CLEIA include a reaction step of reacting a sample (antigen or antibody) and a reagent in a reactor vessel, a separating step (BF separation) for separating a reaction product (bound) and an unreacted substance (free) from each other in the reactor vessel, and a photometric step of measuring the emission quantity of light generated from an immune complex that is generated when each reagent and the sample react with each other.

[Measuring System of Automated Analyzer 1]

The measuring device 2 roughly includes a reactor vessel supplying unit 3, a sample installing unit 4, a reactor vessel transporting unit 5, a sample dispensing unit 6, a reagent cold reserving unit 7, a first reagent dispensing unit 8, a second reagent dispensing unit 9, an immune enzyme reaction unit 10, a first BF separating unit 11, a second BF separating unit 12, a substrate liquid cooler 14, a vessel transfer arm 15, and an emission measuring unit 16.

The reactor vessel supplying unit 3 houses a plurality of reactor vessels (cuvettes) 3a, and supplies the plurality of reactor vessels 3a one at a time to a transfer position. The reactor vessel 3a supplied to the transfer position is transported to the immune enzyme reaction unit 10 by the reactor vessel transporting unit 5. A sample and a prescribed reagent are injected into the reactor vessel 3a transported to the immune enzyme reaction unit 10.

The reactor vessel transporting unit 5 includes an arm and a holding unit. The arm moves up and down in vertical directions and is rotatable around a vertical line that extends through a base end portion of the arm and that serves as a center axis. The holding unit is provided at an end portion of the arm. In the reactor vessel transporting unit 5, the reactor vessel 3a supplied to a supply position of the reactor vessel supplying unit 3 is held by the holding unit, and the arm rotates, so that the reactor vessel 3a is transported to a prescribed position on the immune enzyme reaction unit 10 at a prescribed timing.

The sample installing unit 4 includes a turntable having the form of a substantially cylindrical vessel that is open at one end in an axial direction. The sample installing unit 4 houses a plurality of sample vessels 4a. The sample vessels 4a house samples of blood, urine, or the like, taken from an examinee. The plurality of sample vessels 4a are disposed side by side and apart from each other with prescribed intervals therebetween in a peripheral direction of the sample installing unit 4. The sample installing unit 4 is supported so as to be rotatable along the peripheral direction by a drive mechanism (not shown). The sample installing unit 4 is rotated at a prescribed speed for each prescribed angular range in the peripheral direction by the drive mechanism (not shown). In the embodiment in FIG. 1, the sample vessels 4a that are arranged side by side in the peripheral direction of the sample installing unit 4 are provided in two rows that are apart from each other with a prescribed interval therebetween in a radial direction of the sample installing unit 4. As the sample, a sample diluted by a prescribed diluent may be used.

The sample dispensing unit 6 includes an arm and a probe. The arm moves up and down in vertical directions and is rotatable around a vertical line that extends through a base end portion of the arm and that serves as a center axis. The probe is provided at an end portion of the arm. In the sample dispensing unit 6, the probe sucks the sample in the sample vessel 4a moved to a prescribed position on the sample installing unit 4, and the arm rotates, so that the sample is dispensed into the reactor vessel 3a that is at the prescribed position on the immune enzyme reaction unit 10 at a prescribed timing.

As with the sample installing unit 4, the reagent cold reserving unit 7 includes a turntable having the form of a substantially cylindrical vessel that is open at one end in an axial direction. The reagent cold reserving unit 7 is supported so as to be rotatable along the peripheral direction by a drive mechanism (not shown). The reagent cold reserving unit 7 is rotated in a normal direction or in a reverse direction at a prescribed speed for each prescribed angular range in the peripheral direction thereof by the drive mechanism (not shown).

The reagent cold reserving unit 7 houses a first reagent vessel 7a and a second reagent vessel 7b. The first reagent vessel 7a and the second reagent vessel 7b are disposed side by side apart from each other with a prescribed interval therebetween in the peripheral direction of the reagent cold reserving unit 7. The first reagent vessel 7a houses, as a first reagent, a magnetic reagent composed of magnetic particles that react with a target antigen in the sample. The second reagent vessel 7b houses, as a second reagent, a labeling reagent (enzyme antibody) that reacts with a reaction product in which the magnetic reagent and the antigen in the sample are combined with each other. The interior of the reagent cold reserving unit 7 is maintained at a prescribed temperature by a cold reserving mechanism (not shown). Therefore, the first reagent (magnetic reagent) housed in the first reagent vessel 7a and the second reagent (labeling reagent) housed in the second reagent vessel 7b are kept cool at a prescribed temperature.

The first reagent dispensing unit 8 includes an arm and a probe. The arm moves up and down in vertical directions and is rotatable around a vertical line that extends through a base end portion of the arm and that serves as a center axis. The probe is provided at an end portion of the arm. In the first reagent dispensing unit 8, the probe sucks the first reagent (magnetic reagent) in the first reagent vessel 7a moved to a prescribed position on the reagent cold reserving unit 7, and the arm is rotated, so that the first reagent is dispensed into the reactor vessel 3a that is at the prescribed position on the immune enzyme reaction unit 10 at a prescribed timing.

The structure of the second reagent dispensing unit 9 is the same as the structure of the first reagent dispensing unit 8. In the second reagent dispensing unit 9, a probe sucks the second reagent (labeling reagent) in the second reagent vessel 7b moved to the prescribed position on the reagent cold reserving unit 7, and the arm is rotated, so that the second reagent is dispensed into the reactor vessel 3a that is at the prescribed position on the immune enzyme reaction unit 10 at a prescribed timing.

At the immune enzyme reaction unit 10, an immune reaction between the sample and a prescribed reagent corresponding to analysis items occurs in the reactor vessel 3a disposed in a peripheral direction, and an enzyme reaction between a chemoluminescent substrate and an immune complex generated by the immune reaction occurs. As with the sample installing unit 4, the immune enzyme reaction unit 10 includes a turntable having the form of a substantially cylindrical vessel that is open at one end in an axial direction. The immune enzyme reaction unit 10 is supported so as to be rotatable along the peripheral direction by a drive mechanism (not shown). The immune enzyme reaction unit 10 is rotated at a prescribed speed for each prescribed angular range in the peripheral direction thereof by the drive mechanism (not shown). Here, the immune enzyme reaction unit 10 rotates counterclockwise. In the embodiment in FIG. 1, the reactor vessels 3a that are arranged side by side in the peripheral direction of the immune enzyme reaction unit 10 are set in one row and apart from each other with prescribed intervals therebetween in a radial direction of the immune enzyme reaction unit 10. However, it is possible to provide a row of reactor vessels 3a for the first reagent (described later) and a row of reactor vessels 3a for the second reagent (described later) apart from each other with a prescribed interval therebetween in the radial direction.

When the first reagent dispensing unit 8 dispenses the magnetic reagent into the reactor vessel 3a into which the sample has been injected, the immune enzyme reaction unit 10 stirs a liquid mixture containing the magnetic reagent and the sample by a stirring mechanism (not shown), so that an immune reaction between the magnetic reagent and the antigen in the sample occurs for a certain period of time (primary immune reaction). Next, the immune enzyme reaction unit 10 causes this reactor vessel 3*a* to move to a first magnetism collecting mechanism (magnet 13), so that a reaction product in which the antigen and the magnetic reagent have combined with each other is subjected to a magnetism collecting operation performed by a magnetic force. Then, in this state, the interior of the reactor vessel 3*a* is cleaned to remove any unreacted substances that did not react with the magnetic reagent (primary BF separating operation).

The first magnetism collecting mechanism is fixed to a position that corresponds to the position of the first BF separating unit 11 disposed in the vicinity of an outer peripheral portion of the immune enzyme reaction unit 10. The turntable of the immune enzyme reaction unit 10 includes two layers, that is, a fixed lower layer and a rotatable upper layer. The magnet 13 serving as the first magnetism collecting mechanism is disposed at the turntable at the lower layer, and the reactor vessel 3*a* is disposed at the turntable at the upper layer. The magnet 13 performs the magnetism collecting operation on the reaction product in the reactor vessel 3*a*.

The first BF separating unit 11 includes an arm 25, a nozzle 21 mounted on the arm 25, and a cleaning tank 24. The arm 25 moves up and down in vertical directions and is rotatable around a vertical line that extends through a base end portion of the arm and that serves as a center axis. The arm 25 moves the nozzle 21 to the reactor vessel 3*a* that is at a primary BF separation position at the immune enzyme reaction unit 10, and to the cleaning tank 24 at a nozzle cleaning position at a side of the first BF separating unit 11. At the primary BF separation position, the nozzle 21 discharges a cleaning liquid into the reactor vessel 3*a* into which the sample and the magnetic reagent have been injected and sucks the cleaning liquid to clean the interior of this reactor vessel 3*a*, so that any unreacted substances that did not react with the magnetic reagent are removed (BF cleaning operation).

When the reactor vessel 3*a* is transported to the primary BF separation position, the first BF separating unit 11 performs the primary BF separating operation. By the primary BF separating operation and the BF cleaning operation, the reaction product in which the magnetic reagent and the target antigen in the sample have combined with each other is subjected to the magnetism collecting operation in the reactor vessel 3*a*. Then, when the primary BF separating operation ends, the nozzle 21 is moved to the nozzle cleaning position where the cleaning tank 24 is situated by the arm 25.

After the primary BF separating operation, when the second reagent dispensing unit 9 dispenses a labeling reagent into the reactor vessel 3*a* where the reaction product has remained, the immune enzyme reaction unit 10 stirs the liquid mixture containing the magnetic reagent and the sample by the stirring mechanism (not shown), so that an immune reaction between the reaction product and the labeling reagent occurs for a certain period of time (secondary immune reaction). Next, the immune enzyme reaction unit 10 causes the reactor vessel 3*a* to move to a second magnetism collecting mechanism (not shown), so that an immune complex in which the reaction product and the labeling reagent have combined with each other is subjected to a magnetism collecting operation by a magnetic force. Then, in this state, the interior of the reactor vessel 3*a* is cleaned to remove any unreacted substances that did not react with the labeling reagent (secondary BF separating operation).

The second magnetism collecting mechanism includes a magnet that is the same as the magnet 13 of the first magnetism collecting mechanism, and is fixed to a position that corresponds to the position of the second BF separating unit 12 disposed near the outer peripheral portion of the immune enzyme reaction unit 10. In the embodiment in FIG. 1, the magnet of the second magnetism collecting mechanism is disposed below a nozzle 21 that is at a secondary BF separation position.

The second BF separating unit 12 has a structure that is the same as that of the first BF separating unit 11, and is disposed apart from the first BF separating unit 11 with a prescribed distance therebetween in a peripheral direction. An arm 25 moves up and down in vertical directions and is rotatable around a vertical line that extends through a base end portion of the arm and that serves as a center axis. The arm 25 moves the nozzle 21 to the reactor vessel 3*a* that is at the secondary BF separation position at the immune enzyme reaction unit 10, and to a cleaning tank 24 at a nozzle cleaning position that is situated at a side of the second BF separating unit 12. At the secondary BF separation position, the nozzle 21 discharges a cleaning liquid into the reactor vessel 3*a* into which the labeling reagent has been injected and sucks the cleaning liquid to clean the interior of this reactor vessel 3*a*, so that any excess unreacted substances that did not react with the labeling reagent are removed (BF cleaning operation).

When the reactor vessel 3*a* is transported to the secondary BF separation position, the second BF separating unit 12 performs the secondary BF separating operation. By the secondary BF separating operation and the BF cleaning operation, the immune complex in which the labeling reagent and the reaction product containing the magnetic reagent and the target antigen in the sample have combined with each other is subjected to the magnetism collecting operation in the reactor vessel 3*a*. Then, when the secondary BF separating operation ends, the arm 25 moves the nozzle 21 to the nozzle cleaning position where the cleaning tank 24 is situated.

Here, the nozzle 21 and the cleaning tank 24 are described. The first BF separating unit 11 and the second BF separating unit 12 are commonly described.

Figure 2:
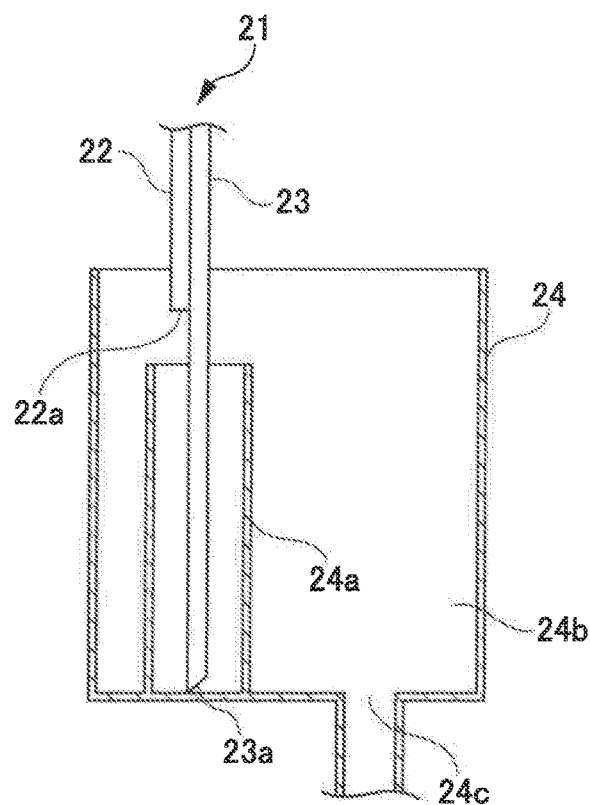
FIG. 2 is a schematic sectional view of a structure of a nozzle and a cleaning tank in FIG. 1.

FIG. 2 is a schematic sectional view of a structure of the nozzle 21 and the cleaning tank 24.

Figure 3A:
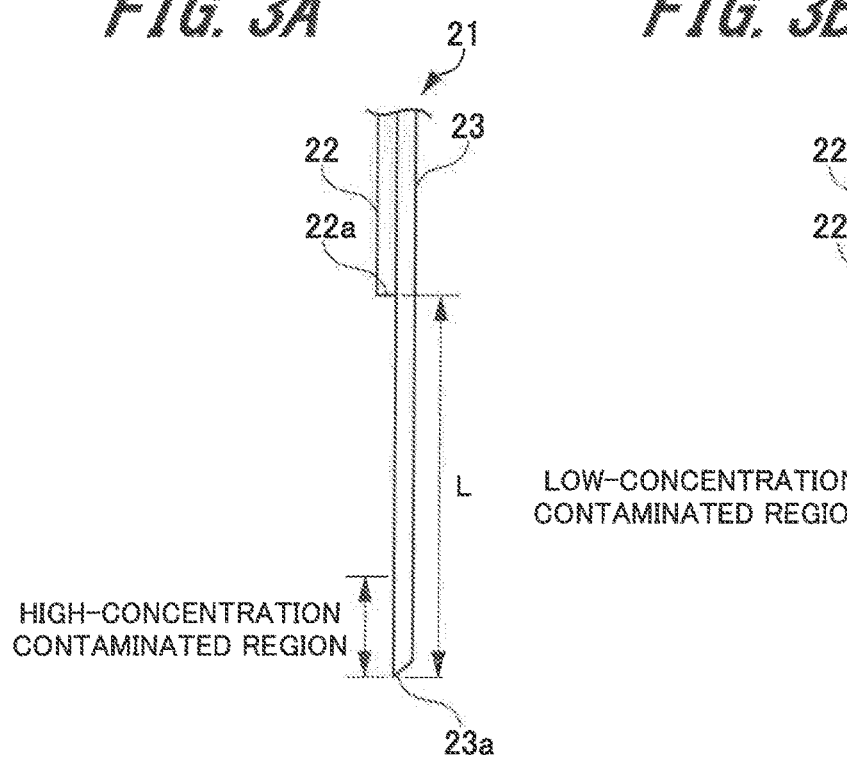
FIGS. 3A and 3B are explanatory views of contaminated regions of a suction nozzle in FIG. 2, with FIG. 3A showing a high-concentration contaminated region and FIG. 3B showing a low-concentration contaminated region.
Figure 3B:
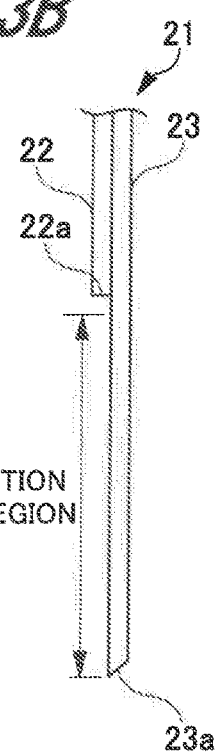

FIG. 3 is an explanatory view of contaminated regions of a suction nozzle of the nozzle 21, with FIG. 3A showing a high-concentration contaminated region and FIG. 3B showing a low-concentration contaminated region.

As shown in FIG. 2, the nozzle 21 includes a discharge nozzle 22 (exemplary discharge unit) that discharges a cleaning liquid and the suction nozzle 23 (exemplary suction unit) that sucks the cleaning liquid. The discharge nozzle 22 and the suction nozzle 23 are disposed so as to contact in parallel in an axial direction. The discharge nozzle 22 has a tubular shape, and an opening portion 22*a* (discharge opening) is formed in a lower end thereof. The suction nozzle 23 has a tubular shape that is longer than the discharge nozzle 22 in the axial direction, and an opening portion 23*a* (suction opening) is formed in a lower end thereof. A lower end side of the nozzle 21 corresponds to a direction in which the nozzle 21 enters a reactor vessel 3*a* or the cleaning tank 24. As shown in FIG. 3, the discharge nozzle 22 and the suction nozzle 23 are formed such that the lower end of the discharge nozzle 22 is separated upwardly from the lower end of the suction nozzle 23 by a distance L (see FIG. 3A).

Here, the distance L is determined such that the lower end of the discharge nozzle 22 is positioned above a liquid surface when the suction nozzle 23 is immersed in a liquid in the reactor vessel 3a and the cleaning tank 24. That is, the distance L between a front end of the discharge nozzle 22 and a front end of the suction nozzle 23 is determined such that, when the nozzle 21 is inserted into the reactor vessel 3a to be cleaned and discharges a cleaning liquid, the cleaning liquid does not reach the discharge nozzle 22. The shape of the cleaning tank 24 is determined in relation to the distance L. In other words, the distance L is determined on the basis of a vessel shape and a cleaning liquid amount required for the actual BF cleaning. When the distance L is determined in this way, the discharge nozzle 22 does not contact liquids other than the cleaning liquid that is discharged from the discharge nozzle 22. A tube is mounted on an upper end portion of the discharge nozzle 22 and an upper end portion of the suction nozzle 23, and the upper end portion of the discharge nozzle 22 and the upper end portion of the suction nozzle 23 are, respectively, connected to a discharge pump and a suction pump (not shown).

The cleaning tank 24 has a substantially quadrangular prism shape or a substantially columnar shape with an opening portion in a top portion thereof. The cleaning tank 24 has a cleaning unit 24a in which a cleaning liquid can accumulate when the nozzle 21 is inserted from thereabove in cleaning the nozzle and an overflow unit 24b into which a cleaning liquid that has overflowed from the cleaning unit 24a flows. A discharge opening 24c is formed in a bottom surface of the overflow unit 24b, and the cleaning liquid that has flown into the overflow unit 24b is discharged via the discharge opening 24c.

Next, parts that are required for cleaning the nozzle 21 are described.

In the automated analyzer 1 to which an immunology analysis device is applied, for example, a sample of approximately 50 to 100 μL exists in the reactor vessel 3a. The high-concentration contaminated region of the suction nozzle 23 is a region corresponding to a portion where the suction nozzle 23 is immersed in a liquid in the reactor vessel 3a, and corresponds to a front end portion of the suction nozzle 23 as shown in FIG. 3A. The height from a lower end of the actual high-concentration contaminated region (opening portion 23a) depends upon the shape of the reactor vessel 3a that is handled. On the other hand, when, in a BF separating step, the reactor vessel 3a is filled up with cleaning liquid, the liquid surface of the cleaning liquid rises up to a position close to the opening portion 22a of the discharge nozzle 22. Therefore, a large portion of the distance L of the suction nozzle 23 becomes the low-concentration contaminated region due to cleaning liquid contaminated at low concentration by dispersion of a contaminant in the reactor vessel 3a. The height from a lower end of the actual low-concentration contaminated region (opening portion 23a) depends upon the shape of the reactor vessel 3a that is handled.

In the present embodiment, these contaminated regions of the nozzle 21 are cleaned. As target values for cleaning, for example, values that are 0.1 ppm or less determined on the basis of immunology analysis are set (contaminant adhered to the nozzle 21 is diluted to $1/10,000,000$ or less by the cleaning).

The description of FIG. 1 is returned to. A substrate liquid dispensing unit 26 is further mounted on the arm 25 of the second BF separating unit 12. The substrate liquid dispensing unit 26 is disposed at a position that is further away from a rotation axis of the arm 25 than the nozzle 21 is. The substrate liquid dispensing unit 26 is connected, via a tube (not shown), to the substrate liquid cooler 14 that houses a substrate liquid and keeps it cool. The substrate liquid dispensing unit 26 dispenses a substrate liquid containing a chemoluminescent substrate that specifically reacts with the labeling reagent into the reactor vessel 3a after the secondary BF separation with respect to the immune complex in which a magnetic reagent, an antigen, and the labeling reagent (enzyme antibody) have combined with each other. Then, the reactor vessel 3a into which the substrate liquid has been injected is transported to a prescribed position by rotating the immune enzyme reaction unit 10. The reactor vessel 3a transported to the prescribed position is transferred to the emission measuring unit 16 by the vessel transfer arm 15.

The emission measuring unit 16 is a photometric unit in which a photomultiplier tube (PMT) 16a is used as a detector, and performs a photometric operation by performing a photocount of emission phenomena produced by the immune complex and the chemoluminescent substrate. That is, the emission quantity of light is measured. A photometric signal corresponding to light beams (emission quantity of light) detected by the emission measuring unit 16 is digitized by an analog-digital converter (not shown). Then, the digitized photometric signal is input to the controlling device 40 via a serial interface (not shown), and is analyzed.

Each unit of the measuring device 2 and the emission measuring unit 16 operate on the basis of an instruction from the controlling device 40.

[Control System and Piping System of Automated Analyzer 1]

Next, a piping system and a control system of the automated analyzer 1 are described.

Figure 4:
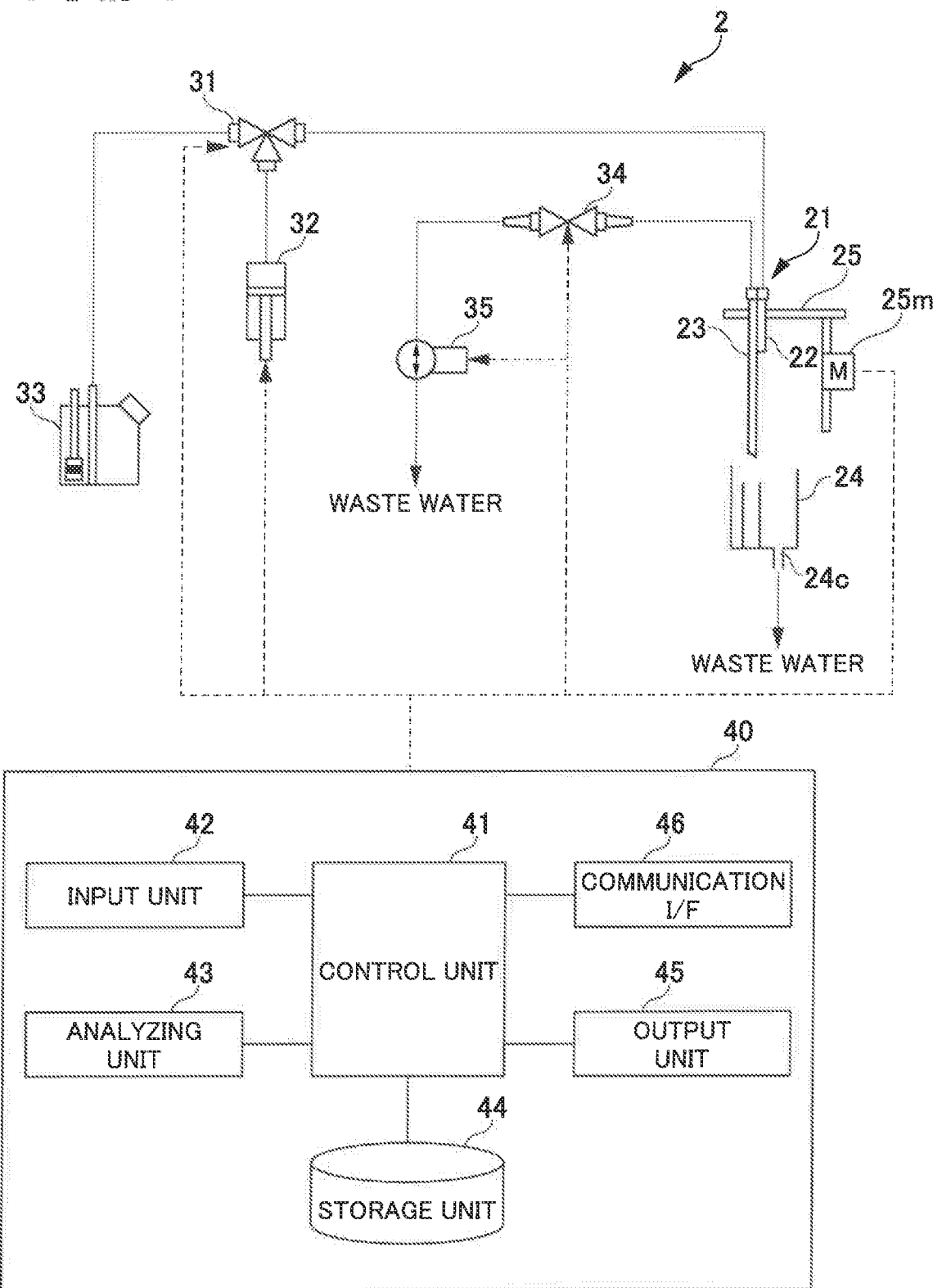
FIG. 4 is a structural view of a control system of the automated analyzer in FIG. 1.

FIG. 4 is a structural view of the piping system and the control system related to cleaning of the nozzle 21 of the automated analyzer 1.

(Piping System)

In the measuring device 2 of the automated analyzer 1, the discharge nozzle 22 is connected to a discharge pump 32 and to a cleaning liquid tank 33 via a discharge electromagnetic valve 31 by a tube. By switching between an open state and a closed state of the discharge electromagnetic valve 31, suction of a cleaning liquid from the cleaning liquid tank 33 to the discharge pump 32 and discharge of the cleaning liquid from the discharge pump 32 to the discharge nozzle 22 are controlled.

The suction nozzle 23 is connected to a suction pump 35 via a suction electromagnetic valve 34 by a tube. The other end of the suction pump 35 is connected to a waste water tank (not shown) in the measuring device 2 or a drain port outside the measuring device 2, provided as waste fluid exits. In general, the suction pump 35 is used by being continuously operated. In this case, the suction is controlled by switching between an open state and a closed state of the suction electromagnetic valve 34.

In the present embodiment, as an example, a syringe pump is used for the discharge pump 32, and a diaphragm pump is used for the suction pump 35. The combination of these pumps may be reversed. Alternatively, a diaphragm pump may be used for the discharge pump 32.

The arm 25 on which the nozzle 21 is mounted is moved vertically by, for example, a pulse motor 25m, provided as a drive mechanism, and is moved horizontally (the BF separation position and the nozzle cleaning position) by a drive mechanism (not shown). The discharge opening 24c of the cleaning tank 24 is connected to a waste water tank (not shown) in the measuring device 2 or a drain port outside the measuring device 2.

The above-described pumps, electromagnetic valves, and drive mechanisms are connected to the controlling device 40 via, for example, a serial interface (not shown).

(Control System)

Next, the controlling device 40 is described.

As shown in FIG. 4, the controlling device 40 includes a control unit 41, an input unit 42, an analyzing unit 43, a storage unit 44, an output unit 45, and a communication interface (in FIG. 4, "communication I/F") 46.

The control unit 41 includes, for example, a CPU (Central Processing Unit), ROM (Read Only Memory) that stores a program and that is not shown, and RAM (Random Access Memory) that is used as a working area of the CPU. The CPU of the control unit 41 reads out the program stored in ROM to RAM, and, in accordance with the program, controls processing and operation of each structural part of the automated analyzer 1. The control unit 41 is electrically connected to the input unit 42, the analyzing unit 43, the storage unit 44, the output unit 45, and the communication interface 46 via a system bus (not shown). By using various programs related to each processing of the automated analyzer 1, the controlling device 40 performs control of a reaction step, a separating step (BF separation), and a photometric step in immunology analysis.

The input unit 42 is a part that inputs, for example, measurement items to the control unit 41; and, for example, a keyboard, mouse, and the like, are used.

The analyzing unit 43 is connected to the emission measuring unit 16 via the control unit 41. On the basis of the light quantity that the emission measuring unit 16 has received, the analyzing unit 43 analyzes, for example, component concentrations of the measurement items of a sample, and outputs the results of the analysis to the control unit 41.

The storage unit 44 is a non-volatile mass-storage device, and stores various pieces of information including, for example, measurement conditions for the respective measurement items of a sample and the results of the analysis of the measurement items of the sample. For the storage unit 44, storage devices such as magnetic disks or SSD (Solid State Drive) are used. The storage unit 44 may also be provided with an auxiliary storage device that is capable of reading information stored in a storage medium, such as an optical disk, a magneto-optical disk, an IC card, or an SD card.

The output unit 45 is formed from a display (display section), a speaker, or a printer. Under the control of the control unit 41, the output unit 45 outputs various pieces of information related to the analysis of a sample. The display displays, for example, the contents of analysis of the sample, and warnings. The input unit 42 and the display section may be realized by a touch panel.

The communication interface 46 is an interface that transmits and receives information in accordance with a prescribed format via a communication network (not shown). For example, a serial interface is used as the communication interface 46.

The control unit 41 outputs instructions to each pump, each electromagnetic valve, and each drive mechanism (described above) via the communication interface 46, and controls a nozzle cleaning process in the separation step in immunology analysis.

[Nozzle Cleaning Process of Automated Analyzer 1]

Next, a nozzle cleaning process of the automated analyzer 1 is described.

In the nozzle cleaning process according to the present embodiment, in order to more effectively clean the high-concentration cleaning region of the suction nozzle 23, first, the high-concentration contaminated region is cleaned by a small amount of cleaning liquid, and, then, the entire low-concentration contaminated region of the suction nozzle 23 is immersed in the cleaning liquid. The longer the time during which the contaminated regions contact the cleaning liquid, the higher the cleaning effect is. At this time, in order to simplify control when cleaning the suction nozzle 23, the discharge of the cleaning liquid by the discharge nozzle 22 is performed only once instead of a plurality of times. A specific nozzle cleaning process procedure is hereunder described with reference to FIGS. 5 to 9.

Figure 5:
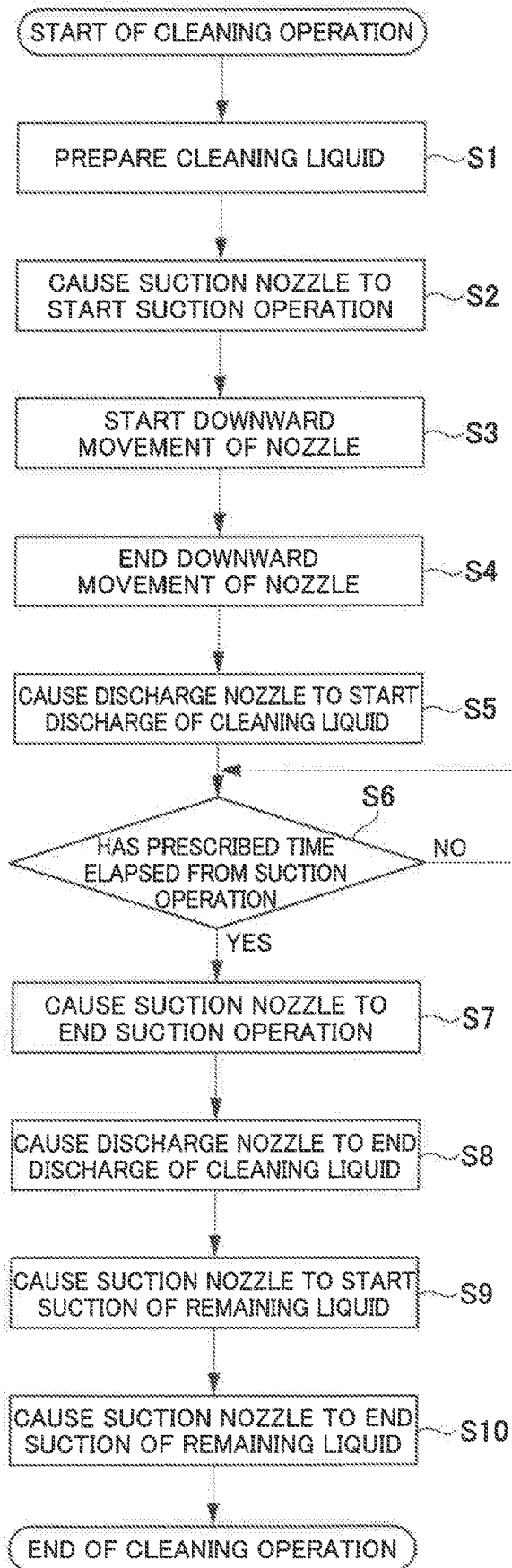
FIG. 5 is a flowchart of a nozzle cleaning process according to the first embodiment of the present invention.

FIG. 5 is a flowchart of the nozzle cleaning process of the automated analyzer 1.

Figure 6:
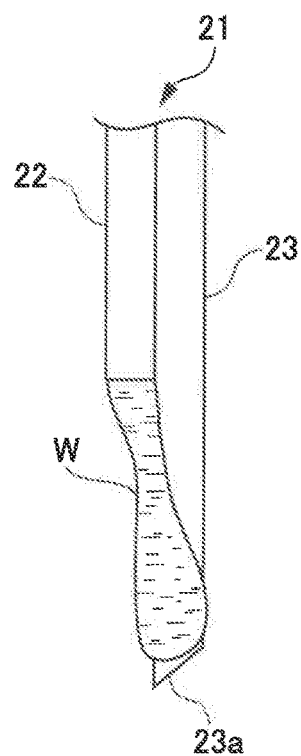
FIG. 6 is an explanatory view of a flow of cleaning liquid discharged from a discharge nozzle according to the first embodiment of the present invention.

FIG. 6 is an explanatory view of a flow of cleaning liquid discharged from the discharge nozzle 22.

Figure 7:
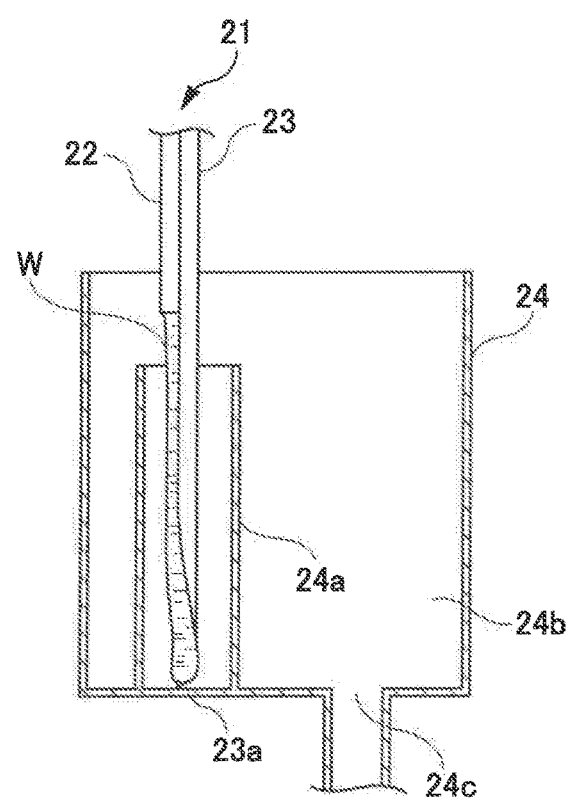
FIG. 7 is an explanatory view of a flow (F1) of cleaning liquid when cleaning the nozzle according to the first embodiment of the present invention.

FIG. 7 is an explanatory view of a flow (F1) of cleaning liquid when cleaning the nozzle according to the first embodiment.

Figure 8:
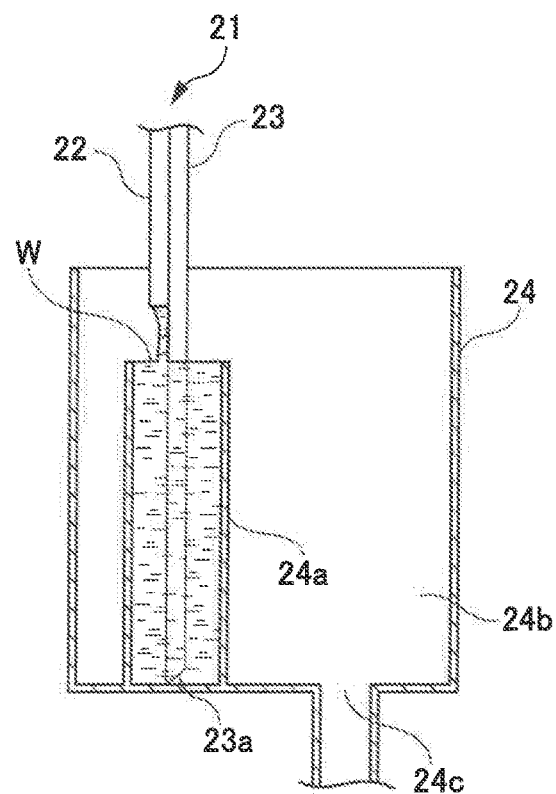
FIG. 8 is an explanatory view of a flow (F2) of the cleaning liquid when cleaning the nozzle according to the first embodiment of the present invention.

FIG. 8 is an explanatory view of a flow (F2) of the cleaning liquid when cleaning the nozzle according to the first embodiment.

Figure 9:
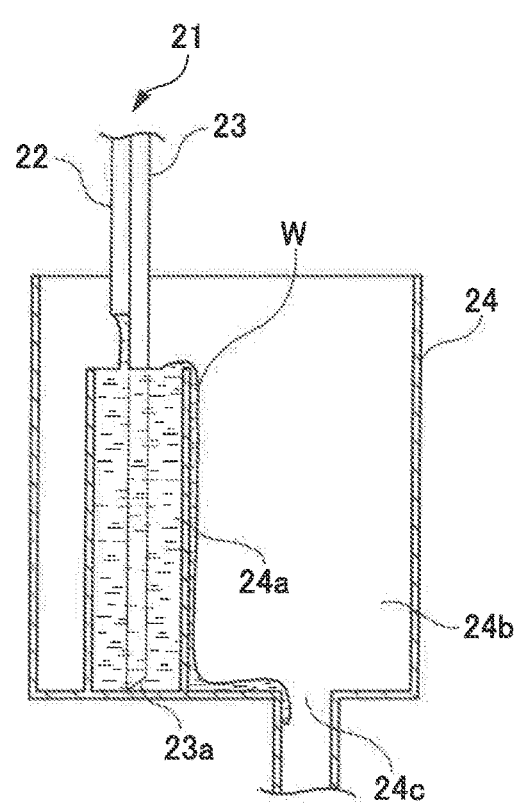
FIG. 9 is an explanatory view of a flow (F3) of the cleaning liquid when cleaning the nozzle according to the first embodiment of the present invention.

FIG. 9 is an explanatory view of a flow (F3) of the cleaning liquid when cleaning the nozzle according to the first embodiment.

As shown in FIG. 5, after the primary BF separation (or the secondary BF separation) has ended, first, the control unit 41 of the controlling device 40 causes the nozzle 21 to move to a location above the nozzle cleaning position, that is, the cleaning tank 24 by using the arm 25 of the first BF separating unit 11 (or the second BF separating unit 12). Then, the control unit 41 causes a nozzle cleaning operation that uses the nozzle 21 and the cleaning tank 24 to be started.

When the nozzle cleaning operation is started, the control unit 41 causes a cleaning liquid used in cleaning the nozzle 21 to be prepared (Step S1). More specifically, the control unit 41 controls the discharge electromagnetic valve 31 and the discharge pump 32 and causes the discharge pump 32 to suck the cleaning liquid from the cleaning liquid tank 33.

Next, the control unit 41 controls the suction electromagnetic valve 34 and the suction pump 35 and causes the suction nozzle 23 to start a suction operation (first time) (Step S2).

Next, the control unit 41 causes the nozzle 21 to start moving downward towards the cleaning tank 24 (Step S3). Then, when the opening portion 23a of the suction nozzle 23 reaches a bottom surface of the cleaning unit 24a in the cleaning tank 24, the control unit 41 causes the downward movement of the nozzle 21 to end and the position of the nozzle 21 (Step S4) to be fixed. By contacting the opening portion 23a of the suction nozzle 23 with the bottom surface of the cleaning unit 24a, it is possible to suck all of the cleaning liquid accumulated in the cleaning unit 24a when the cleaning liquid (described below) is sucked. When the opening portion 23a of the suction nozzle 23 reaches the vicinity of the bottom surface of the cleaning unit 24a, the control unit 41 may cause the downward movement of the nozzle 21 to end. If, in a state in which the opening portion 23a of the suction nozzle 23 is in the vicinity of the bottom surface, the cleaning liquid that exists at the bottom surface can be absorbed from the opening portion 23a, it can be said that the state in which the opening portion 23a is in the vicinity of the bottom surface is a state in which the opening portion 23a has substantially reached the bottom surface.

Next, the control unit 41 controls the discharge electromagnetic valve 31 and the discharge pump 32, and causes a discharge operation in which the discharge nozzle 22 discharges the cleaning liquid from the opening portion 22a to be started (Step S5). Since the discharge nozzle 22 and the suction nozzle 23 are formed in close contact with each other, as shown in FIG. 6, the cleaning liquid W discharged from the opening portion 22a of the discharge nozzle 22 runs down an outer peripheral surface of the suction nozzle 23. The flow velocity of the cleaning liquid that is discharged from the discharge nozzle 22 is adjusted to a value suitable for allowing the cleaning liquid to run down the outer peripheral surface of the suction nozzle 23. Since the suction nozzle 23 continuously continues the suction operation, the cleaning liquid W that runs down the outer peripheral surface of the suction nozzle 23 is successively sucked by the opening portion 23a of the suction nozzle 23. By this operation, first, the high-concentration contaminated region (see FIG. 3A) at the front end portion of the suction nozzle 23 is cleaned.

Here, the discharge amount per unit time of the cleaning liquid discharged by the discharge nozzle 22 and the suction amount per unit time of the cleaning liquid sucked by the suction nozzle 23 has the relationship of "discharge amount-≤suction amount". Since all of the cleaning liquid W discharged from the discharge nozzle 22 is sucked from the opening portion 23a of the suction nozzle 23, the discharged cleaning liquid W does not accumulate in the cleaning unit 24a of the cleaning tank 24 (see FIG. 7). Therefore, the inside of the cleaning unit 24a is kept in a clean state.

During this time, the control unit 41 determines whether or not a prescribed time has elapsed from the start of the suction operation performed by the suction nozzle 23 (Step S6). The time is measured by using a clock signal that is output by the CPU (not shown) of the control unit 41. Alternatively, the controlling device 40 may be provided with a timer. When it is determined that the prescribed time has not elapsed from the start of the suction operation performed by the suction nozzle 23, the control unit 41 continues the determination process. The prescribed time is at least the time taken for the cleaning liquid W required for cleaning the high-concentration contaminated region of the suction nozzle 23 to be discharged by the discharge nozzle 22.

On the other hand, when, in Step S5, it is determined that the prescribed time has elapsed from the start of the suction operation performed by the suction nozzle 23, the control unit 41 causes the suction operation performed by the suction nozzle 23 to end (Step S7). After the cleaning liquid W required for cleaning the high-concentration contaminated region of the suction nozzle 23 has been discharged, the suction operation performed by the suction nozzle 23 temporarily ends, and the cleaning liquid W is continuously discharged from the discharge nozzle 22. Therefore, the cleaning liquid W discharged from the discharge nozzle 22 accumulates in the cleaning unit 24a (see FIG. 8). At this time, since the positional relationship between the discharge nozzle 22 and the suction nozzle 23 is determined such that the low-concentration contaminated region (FIG. 3B) of the suction nozzle 23 completely enters the cleaning unit 24a, the entire low-concentration contaminated region of the suction nozzle 23 is immersed in the cleaning liquid W in the cleaning unit 24a. Excess cleaning liquid W overflows into the overflow unit 24b, and is discharged from the discharge opening 24c (see FIG. 9).

Next, after the entire low-concentration contaminated region of the suction nozzle 23 has been immersed in the cleaning liquid W, the control unit 41 causes the cleaning-liquid discharge operation performed by the discharge nozzle 22 to end (Step S8). At least the liquid amount of the cleaning liquid W that allows the entire low-concentration contaminated region of the suction nozzle 23 to be immersed in the cleaning liquid W is predetermined. The control unit 41 controls the discharge electromagnetic valve 31 and the discharge pump 32 on the basis of the predetermined liquid amount. The suction operation ending process in Step S7 and the discharge operation ending process in Step S8 may temporally vary slightly as long as the cleaning liquid required for cleaning the low-concentration contaminated region can be accumulated. The discharge of the cleaning liquid performed by the discharge nozzle 22 may be ended when any sensor detects that the cleaning liquid W has overflowed from the cleaning unit 24a.

Thereafter, the control unit 41 causes the suction nozzle 23 to start the suction operation again (second time) to suck all of the cleaning liquid W (remaining liquid) accumulated in the cleaning unit 24a (Step S9). After all of the cleaning liquid W accumulated in the cleaning unit 24a has been sucked by the suction nozzle 23, the control unit 41 causes the suction operation performed by the suction nozzle 23 to end (Step S10). When the control unit 41 causes the process in Step S10 to end, the nozzle cleaning operation ends.

In the above-described first embodiment, first, the front end portion (high-concentration contaminated region) of the suction nozzle 23 contaminated with high concentration is cleaned with a small amount of cleaning liquid W, and the cleaning liquid W used in the cleaning is sucked by the suction nozzle 23. Next, the entire suction nozzle 23 contaminated with low concentration (low-concentration contaminated region) is cleaned with the cleaning liquid W accumulated in the cleaning unit 24a, and the cleaning liquid W used in the cleaning is sucked by the suction nozzle 23. The cleaning liquid W that is discharged from above the high-concentration contaminated region of the suction nozzle 23 (the opening portion 22a of the discharge nozzle 22) flows along the high-concentration contaminated region of the suction nozzle 23 and is sucked from therebelow (the opening portion 23a), so that the time of contact of the high-concentration contaminated region with the cleaning liquid W can be made relatively longer than the time of contact of the low-concentration contaminated region with the cleaning liquid W. Therefore, cleaning power with respect to the high-concentration contaminated region is increased. Further, the cleaning liquid W used in cleaning the high-concentration contaminated region on the lower end portion of the suction nozzle 23 does not accumulate in the cleaning unit 24a. Therefore, the cleaning liquid W that is accumulated in the cleaning unit 24a and used in cleaning the low-concentration contaminated region of the suction nozzle 23 is almost never contaminated by the cleaning liquid W used in cleaning the high-concentration contaminated region. Consequently, according to the first embodiment, a cleaning effect that is higher than before is provided.

Figure 10:
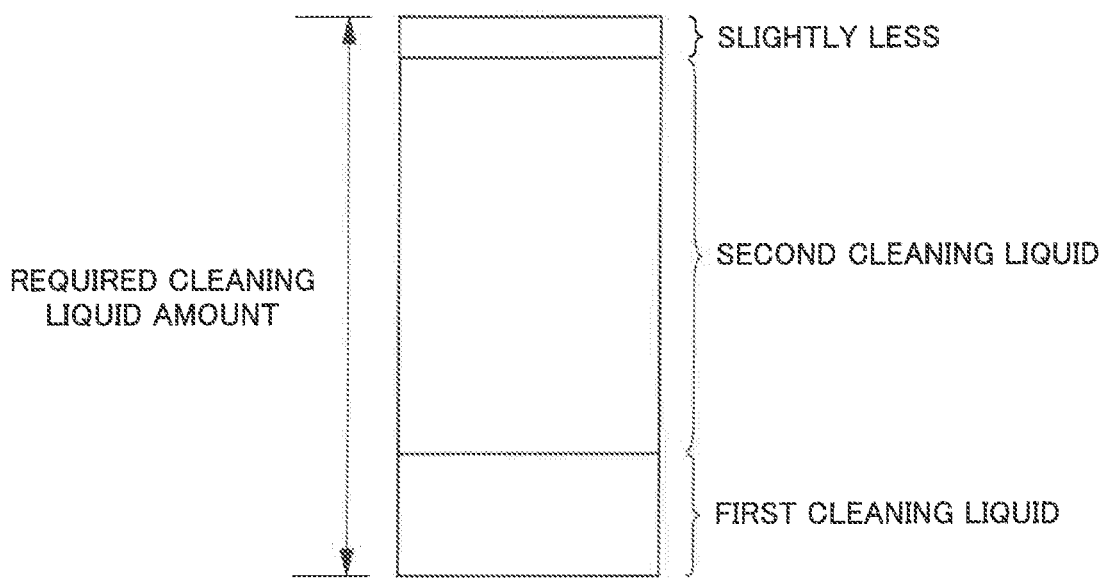
FIG. 10 is an explanatory view showing a relationship between a required cleaning liquid amount and cleaning liquid amounts in a related art.
Figure 11:
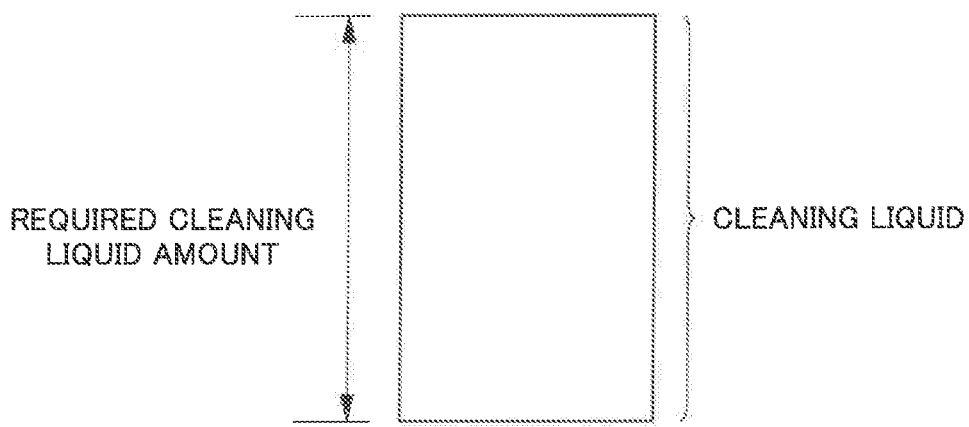
FIG. 11 is an explanatory view showing a relationship between a required cleaning liquid amount and a cleaning liquid amount according to the first embodiment of the present invention.

In addition, according to the first embodiment, a "required cleaning liquid amount" (see FIG. 10) required for the nozzle cleaning described in PTL 1 need not be calculated. A cleaning liquid of an amount that is greater than or equal to a predetermined certain amount may be discharged for the cleaning. That is, in the present embodiment, as shown in FIG. 11, the required cleaning liquid amount is the cleaning liquid amount used in the actual cleaning. Therefore, complicated settings (calculations) need not be performed, as a result of which the liquid amount of cleaning liquid used in the nozzle cleaning can be easily determined.

In the nozzle cleaning described in PTL 1, it is necessary to perform control such that "the second cleaning liquid amount that is discharged is slightly smaller than the difference between the required cleaning liquid amount and the first cleaning liquid amount". This is to, since a syringe nozzle (syringe pump) is used in sucking waste fluid, reliably suck waste fluid in the cleaning tank. On the basis of this thinking, since a pump for continuously feeding a liquid is used in discharging the cleaning liquid, control for performing discharge such that the first cleaning liquid amount and the second cleaning liquid amount become prescribed amounts becomes very complicated. In addition, since a syringe pump is used for sucking the waste fluid after the cleaning, it is necessary to perform a complicated setting (calculation) to "make the second cleaning liquid amount that is discharged slightly smaller than the difference between the required cleaning liquid amount and the first cleaning liquid amount", and control thereof is also complicated. In contrast, when a syringe pump that can continuously feed a liquid is used in sucking waste fluid after the cleaning as in the present embodiment, it is not necessary to perform complicated control to make "the cleaning liquid discharge amount slightly smaller than the required cleaning liquid amount".

In the nozzle cleaning described in PTL 1, the discharge of the cleaning liquid is performed at least two times, and, as described above, the method of determining each discharge amount is also complicated. In contrast, in the present embodiment, for one nozzle cleaning operation, the cleaning liquid W of an amount greater than or equal to a predetermined certain amount is only discharged from the discharge nozzle 22 once to provide the same cleaning effect as that when a cleaning liquid is discharged a plurality of times and to simplify a nozzle cleaning step.

2. Second Embodiment

In the first embodiment, a structure in which the high-concentration contaminated region and the low-concentration contaminated region of the suction nozzle 23 are cleaned in turns by controlling the suction operation performed by the suction nozzle 23 while discharging a cleaning liquid from the discharge nozzle 22 is described. Actually, for example, due to the effects of residual pressure after closing the suction electromagnetic valve 34 or a delay in the opening and closing of the suction electromagnetic valve 34, part of the cleaning liquid that is subsequently discharged after cleaning the high-concentration contaminated region is sucked by the suction nozzle 23, as a result of which a phenomenon in which the cleaning liquid amount required for cleaning the low-concentration contaminated region does not accumulate in the cleaning unit 24a may occur.

The second embodiment is related to a nozzle cleaning process for preventing such a phenomenon. The structures of a control system and a piping system are the same as those in the automated analyzer 1 according to the first embodiment. In the second embodiment, after starting a nozzle cleaning operation, the nozzle 21 starts to move downward, and discharge and suction of cleaning liquid are performed before the downward movement of the nozzle 21 ends. A specific nozzle cleaning process procedure according to the second embodiment is hereunder described with reference to FIGS. 12 to 16.

Figure 12:
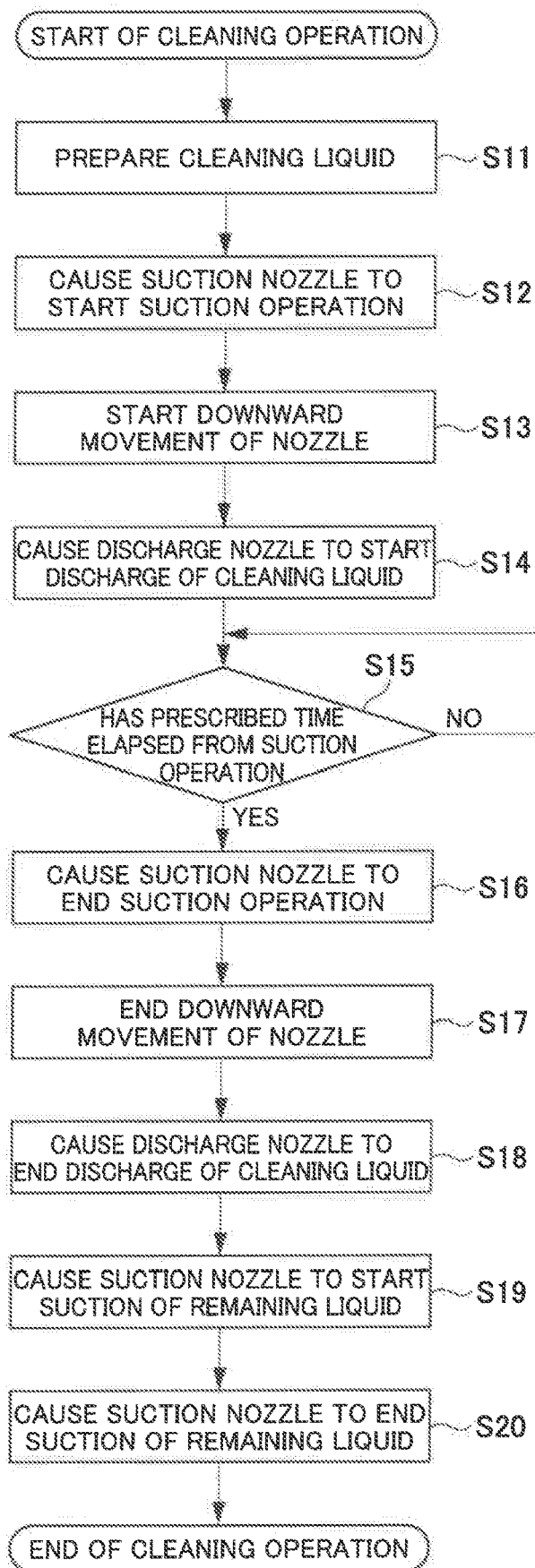
FIG. 12 is a flowchart of a nozzle cleaning process according to a second embodiment of the present invention.

FIG. 12 is a flowchart of the nozzle cleaning process according to the second embodiment.

Figure 13:
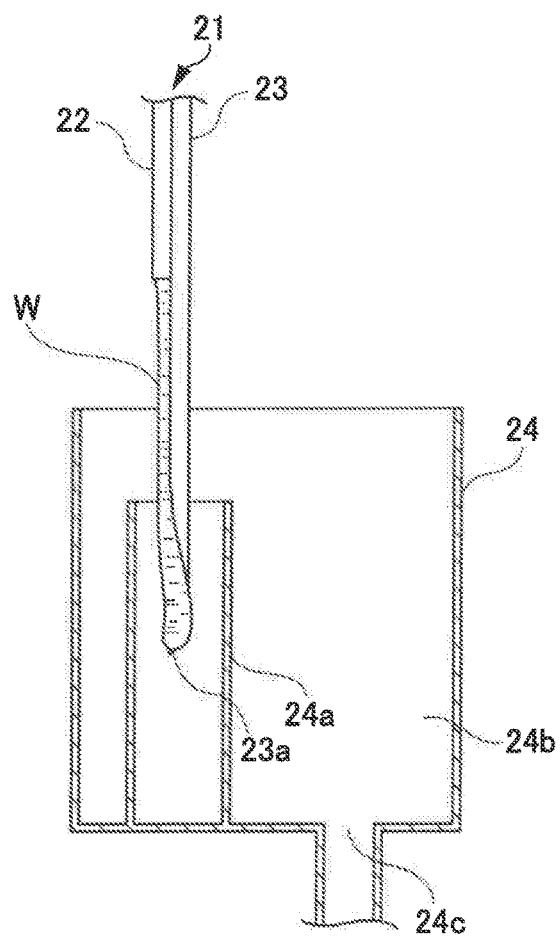
FIG. 13 is an explanatory view of a flow (F1) of cleaning liquid when cleaning a nozzle according to the second embodiment of the present invention.

FIG. 13 is an explanatory view of a flow (1) of cleaning liquid when cleaning the nozzle according to the second embodiment.

Figure 14:
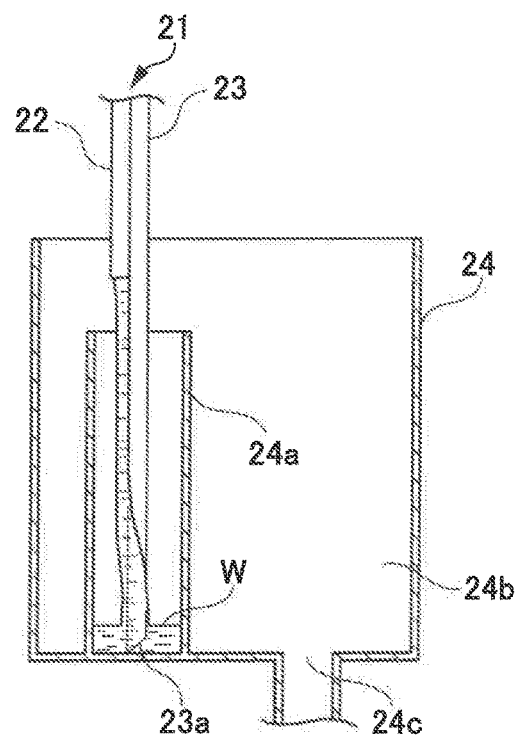
FIG. 14 is an explanatory view of a flow (F2) of the cleaning liquid when cleaning the nozzle according to the second embodiment of the present invention.

FIG. 14 is an explanatory view of a flow (2) of the cleaning liquid when cleaning the nozzle according to the second embodiment.

Figure 15:
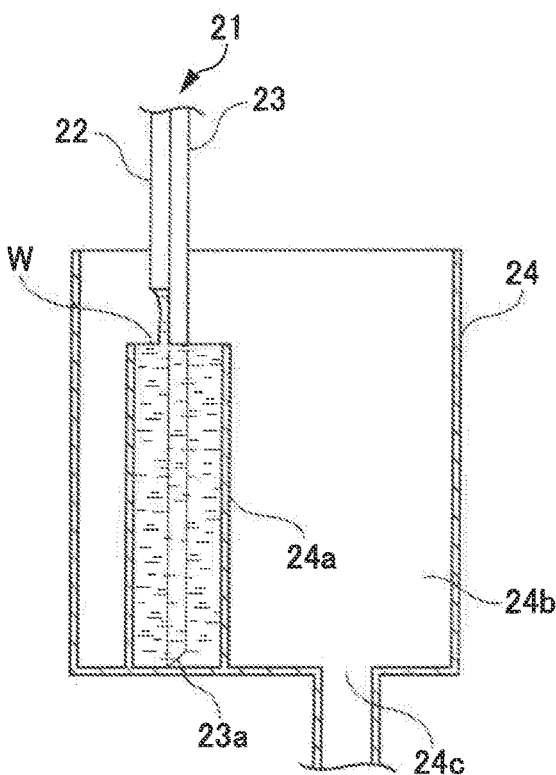
FIG. 15 is an explanatory view of a flow (F3) of the cleaning liquid when cleaning the nozzle according to the second embodiment of the present invention.

FIG. 15 is an explanatory view of a flow (3) of the cleaning liquid when cleaning the nozzle according to the second embodiment.

Figure 16:
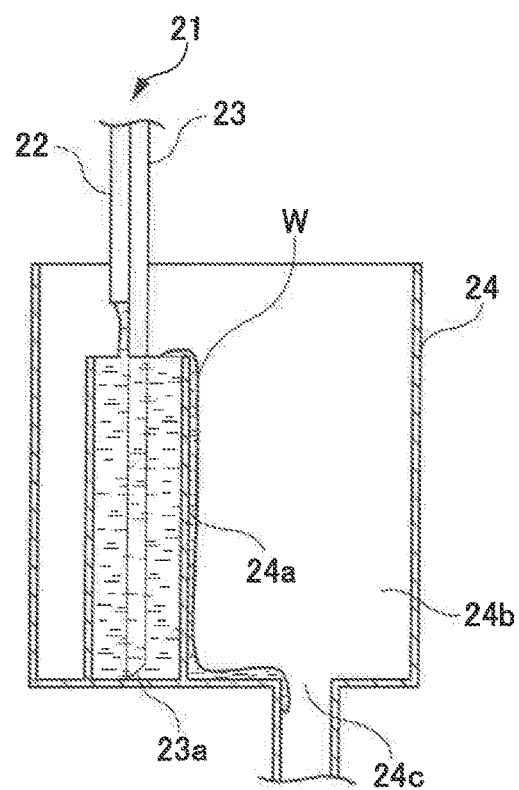
FIG. 16 is an explanatory view of a flow (F4) of the cleaning liquid when cleaning the nozzle according to the second embodiment of the present invention.

FIG. 16 is an explanatory view of a flow (4) of the cleaning liquid when cleaning the nozzle according to the second embodiment.

Of Steps S11 to S20 in FIG. 12, Step S11 corresponds to Step S1 in FIG. 5, Steps S14 and S15 correspond to Steps S5 and S6 in FIG. 5, and Steps S18 to S20 correspond to Steps S8 to S10 in FIG. 5. A description is hereunder given while focusing on the differences between FIGS. 12 and 5.

As shown in FIG. 12, when the nozzle cleaning operation is started, first, the control unit 41 causes a cleaning liquid to be prepared (Step S11). Then, the control unit 41 causes the nozzle 21 to start moving downward towards the cleaning tank 24 (Step S12). The control unit 41 causes the suction nozzle 23 to start a suction operation (first time) at the same time as or subsequently to the downward movement of the nozzle 21 (Step S13). The suction nozzle 23 may start the suction operation before the nozzle 21 moves downward.

Next, the control unit 41 causes a discharge operation in which the discharge nozzle 22 discharges the cleaning liquid from the opening portion 22a to be started (Step S14). Immediately after starting the discharge of the cleaning liquid, the opening portion 23a of the suction nozzle 23 has not yet reached the bottom surface of the cleaning unit 24a in the cleaning tank 24. Therefore, the cleaning liquid discharged from the opening portion 22a of the discharge nozzle 22 runs down the outer peripheral surface of the suction nozzle 23, and is sucked from the opening portion 23a of the suction nozzle 23 as it is (see FIG. 13). By this operation, first, the high-concentration contaminated region (FIG. 3A) on the front end portion of the suction nozzle 23 is cleaned. A high-concentration contaminant adhered to the front end portion of the suction nozzle 23 is sucked from the opening portion 23a of the suction nozzle 23 without entering the cleaning tank 24. Therefore, it is possible to increase the efficiency with which the low-concentration contaminated region (FIG. 3B) of the suction nozzle 23 is cleaned, which cleaning is subsequently performed.

Here, as in the first embodiment, the discharge amount of the cleaning liquid discharged by the discharge nozzle 22 and the suction amount of the cleaning liquid sucked by the suction nozzle 23 has the relationship of "discharge amount-≤suction amount". Therefore, since all of the cleaning liquid W discharged from the discharge nozzle 22 and running down the outer peripheral surface of the suction nozzle 23 is sucked from the opening portion 23a of the suction nozzle 23, the cleaning liquid W does not flow to the cleaning unit 24a of the cleaning tank 24. Therefore, the inside of the cleaning unit 24a is kept in a clean state.

During this time, the control unit 41 determines whether or not a prescribed time has elapsed from the start of the suction operation performed by the suction nozzle 23 (Step S15). When it is determined that the prescribed time has not elapsed from the start of the suction operation performed by the suction nozzle 23, the control unit 41 continues the determination process.

On the other hand, when, in Step S15, it is determined that the prescribed time has elapsed from the start of the suction operation performed by the suction nozzle 23, the control unit 41 temporarily ends the suction operation performed by the suction nozzle 23 (Step S16). Thereafter, when the opening portion 23a of the suction nozzle 23 reaches the bottom surface of the cleaning unit 24a of the cleaning tank 24, the control unit 41 causes the downward movement of the nozzle 21 to end and the position of the nozzle 21 to be fixed (Step S17). In this way, the downward movement of the nozzle 21, the discharge operation performed by the discharge nozzle 22, and the suction operation performed by the suction nozzle 23 are performed such that there is at least partial temporal overlap therebetween.

When the suction operation performed by the suction nozzle 23 temporarily ends, the cleaning liquid W discharged from the discharge nozzle 22 accumulates in the cleaning unit 24a (see FIG. 14), and the entire low-concentration contaminated region (FIG. 3B) of the suction nozzle 23 is immersed in the cleaning liquid W in the cleaning unit 24a (see FIG. 15). Excess cleaning liquid W overflows into the overflow unit 24b, and is discharged from the discharge opening 24c (see FIG. 16).

Here, the suction operation performed by the suction nozzle 23 ends before the nozzle 21 reaches the bottom surface of the cleaning unit 24a. Therefore, before the cleaning liquid W accumulates in the cleaning unit 24a, the effects of residual pressure after closing the suction electromagnetic valve 34 or a delay in the opening and closing of the suction electromagnetic valve 34 are eliminated, so that suction of part of the cleaning liquid W accumulated in the cleaning unit 24a by the suction nozzle 23 does not occur. Therefore, it is possible to prevent the cleaning liquid amount required for cleaning the low-concentration contaminated region of the suction nozzle 23 from becoming insufficient. Since the cleaning liquid W has not yet accumulated in the cleaning unit 24a immediately after the nozzle 21 has reached the bottom surface of the cleaning unit 24a, the suction operation ending process in Step S16 and the downward movement ending process in Step S17 may temporally vary slightly.

Next, after the entire low-concentration contaminated region of the suction nozzle 23 has been immersed in the cleaning liquid W, the control unit 41 causes the discharge operation of the cleaning liquid performed by the discharge nozzle 22 to end (Step S18). Thereafter, the control unit 41 causes the suction nozzle 23 to start the suction operation again (second time) to suck all of the cleaning liquid W (remaining liquid) accumulated in the cleaning unit 24a (Step S19). Then, after all of the cleaning liquid W accumulated in the cleaning unit 24a has been sucked by the suction nozzle 23, the control unit 41 causes the suction operation performed by the suction nozzle 23 to end (Step S20). When the control unit 41 causes the process in Step S20 to end, the nozzle cleaning operation ends.

In the above-described second embodiment, as in the first embodiment, first, the front end portion (high-concentration contaminated region) of the suction nozzle 23 is cleaned with a small amount of cleaning liquid W, and the cleaning liquid W used in the cleaning is sucked by the suction nozzle 23. Next, the entire suction nozzle 23 (low-concentration contaminated region) is cleaned with the cleaning liquid W accumulated in the cleaning unit 24a, and the cleaning liquid W used in the cleaning is sucked by the suction nozzle 23. The high-concentration contaminated region of the suction nozzle 23 is cleaned in the air, and the cleaning liquid W used in cleaning the high-concentration contaminated region does not contact the cleaning unit 24a. Therefore, the cleaning liquid W accumulated in the cleaning unit 24a and used in cleaning the low-concentration contaminated region of the suction nozzle 23 is not contaminated by the cleaning liquid W used in cleaning the high-concentration contaminated region. Consequently, as with the first embodiment, the second embodiment provides a higher cleaning effect than before.

Further, in the second embodiment, the suction operation performed by the suction nozzle 23 ends before the nozzle 21 reaches the bottom surface of the cleaning unit 24a. Therefore, before the cleaning liquid W accumulates in the cleaning unit 24a, the effects of residual pressure after closing the suction electromagnetic valve 34 or a delay in the opening and closing of the suction electromagnetic valve 34 are eliminated. Thus, suction of part of the cleaning liquid W accumulated in the cleaning unit 24a by the suction nozzle 23 does not occur, and it is possible to prevent the cleaning liquid amount required for cleaning the low-concentration contaminated region of the suction nozzle 23 from becoming insufficient.

In the second embodiment, as with the first embodiment, for one nozzle cleaning operation, the cleaning liquid W of an amount greater than or equal to a predetermined certain amount is only discharged from the discharge nozzle 22 once to provide the same cleaning effect as that when a cleaning liquid is discharged a plurality of times and to simplify a nozzle cleaning step.

3. Third Embodiment

In the above-described second embodiment, the suction and the discharge of the cleaning liquid W are performed while the nozzle 21 is moved downward towards the cleaning tank 24 (cleaning unit 24a), and the suction finally ends with the nozzle 21 in contact with the bottom surface of the cleaning unit 24a. However, when the cleaning liquid W is discharged from the discharge nozzle 22 in the air above the cleaning tank 24, depending upon the distance from the bottom surface of the cleaning tank 24 to the front end (opening portion 23a) of the suction nozzle 23, the cleaning liquid W running down the suction nozzle 23 may be scattered to the outside of the cleaning tank 24. Therefore, in the third embodiment, with at least the front end of the suction nozzle 23 in the cleaning tank 24 (cleaning unit 24a) and at a height at which the suction nozzle 23 does not contact the bottom surface of the cleaning unit 24a, the first discharge and suction of the cleaning liquid W are performed. The phrase "with . . . the front end of the suction nozzle 23 in the cleaning unit 24a" means "with the front end being at the same height or below an uppermost portion of the cleaning unit 24a".

More specifically, after the nozzle 21 has started moving downward, with the front end of the suction nozzle 23 in the cleaning unit 24a and at a height at which the front end of the suction nozzle 23 does not contact the bottom surface of the cleaning unit 24a, the control unit 41 causes the nozzle 21 to temporarily stop. In this state, the control unit 41 causes a discharge operation performed by the discharge nozzle 22 and a suction operation performed by the suction nozzle 23 (first time) to be started. In this state, as with the case in which the cleaning liquid W is discharged and sucked in the air while the nozzle 21 is moved downward in the second embodiment, the front end of the suction nozzle 23 is not in contact with the bottom surface of the cleaning unit 24a, so that the effects of residual pressure are suppressed. After a prescribed time has elapsed from the start of the suction operation performed by the suction nozzle 23, the control unit 41 causes the suction operation performed by the suction nozzle 23 to end.

Next, the control unit 41 causes the nozzle 21 to move downward again until the front end of the suction nozzle 23 reaches the bottom surface of the cleaning unit 24*a* or the vicinity thereof. Then, as in the second embodiment, after the entire low-concentration contaminated region of the suction nozzle 23 has been immersed in the cleaning liquid, the control unit 41 causes the discharge operation performed by the discharge nozzle 22 to end. Thereafter, the control unit 41 causes the suction operation (second time) performed by the suction nozzle 23 to start again, and, after all of the cleaning liquid W accumulated in the cleaning unit 24*a* has been sucked by the suction nozzle 23, causes the suction operation performed by the suction nozzle 23 to end.

In the above-described third embodiment, as in the second embodiment, since, during the first suction operation performed by the suction nozzle 23, the front end of the suction nozzle 23 does not contact the bottom surface of the cleaning unit 24*a*, it is possible to clean the suction nozzle 23 while suppressing the effects of residual pressure. Further, in the third embodiment, since the discharge and the suction are performed with at least the front end of the suction nozzle 23 in the cleaning tank 24 (cleaning unit 24*a*), it is possible to prevent the cleaning liquid W discharged from the discharge nozzle 22 and running down the suction nozzle 23 from being scattered to the outside of the cleaning tank 24.

According to the above-described first to third embodiments, it is not necessary to perform complicated cleaning liquid amount settings and complicated control of discharge and suction of cleaning liquid as they are performed in the related art, so that it is possible to realize higher cleaning efficiency than before by performing simpler control.

4. Modifications

Figure 17:
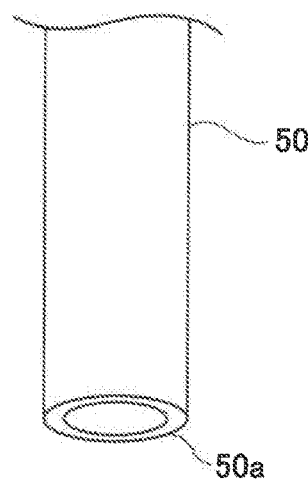
FIG. 17 shows an exemplary front end shape of a suction nozzle.

In the first to third embodiments, the suction nozzle 23 inserted in a reactor vessel 3*a* and the cleaning tank 24 is positioned such that the front end portion (opening portion) thereof contacts a bottom surface of the reactor vessel 3*a* or the bottom surface of the cleaning unit 24*a* of the cleaning tank 24. A suction nozzle 50 shown in FIG. 17 is such that the shape of an opening portion 50*a* at a front end thereof has a planar shape that is perpendicular to an axial direction. As shown in FIG. 17, when the shape of the front end of the suction nozzle 23 has a planar shape that is perpendicular to the axial direction, the front end closely contacts the bottom surface of the reactor vessel 3*a* or the bottom surface of the cleaning unit 24*a*, and sucking force is reduced. Therefore, this is not desirable. Consequently, modifications of the shape of the front end for increasing the suction force of the suction nozzle 23 are described with reference to FIGS. 18 to 21.

Figure 18:
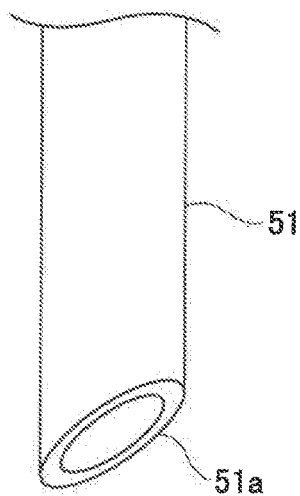
FIG. 18 shows a front end shape of a suction nozzle according to a first modification.

FIG. 18 shows a front end shape of a suction nozzle according to a first modification.

In the suction nozzle 51 shown in FIG. 18, an opening portion 51*a* at the front end thereof has a planar shape having a certain angle with respect to an axial direction. In the case in which the opening portion 51*a* has a planar shape that is oblique with respect to the axial direction in this way, when a front end portion of the suction nozzle 51 is brought into contact with the bottom surface of the reactor vessel 3*a* or the bottom surface of the cleaning unit 24*a*, a gap is formed. Therefore, suction force is not reduced. Consequently, it is possible to reliably suck any liquid remaining at the bottom surface until the end. The shape of the opening portion 23*a* of the suction nozzle 23 used in the first to third embodiments is the same as the shape of the opening portion 51*a* of the suction nozzle 51.

Figure 19:
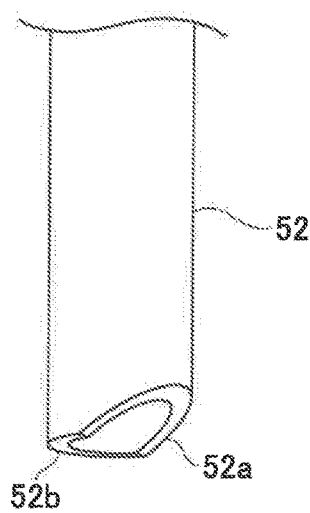
FIG. 19 shows a front end shape of a suction nozzle according to a second modification.

FIG. 19 shows a front end shape of a suction nozzle according to a second modification.

The suction nozzle 52 shown in FIG. 19 has an opening portion 52*a* having an oblique planar shape as in FIG. 18 and an opening portion 52*b* having a planar shape formed by cutting part of the opening portion 52*a* by a plane that is perpendicular to an axial direction. As with the suction nozzle 50 in FIG. 18, the suction nozzle 52 according to the second modification is such that a gap is formed when a front end portion of the suction nozzle 23 is brought into contact with the bottom surface of the reactor vessel 3*a* or the bottom surface of the cleaning unit 24*a*. Therefore, suction force is not reduced. Further, when the front end portion of the suction nozzle 52 contacts the bottom surface of the reactor vessel 3*a* or the bottom surface of the cleaning unit 24*a*, the actual opening that can suck a liquid is smaller than that of the suction nozzle 51 in FIG. 18. Therefore, when sucking a cleaning liquid, it is possible to use more of the surface tension of the cleaning liquid and reduce the amount of air that is sucked. Therefore, the suction operation of the cleaning liquid by the suction nozzle 52, that is, the suction amount of the cleaning liquid is stabilized.

Figure 20:
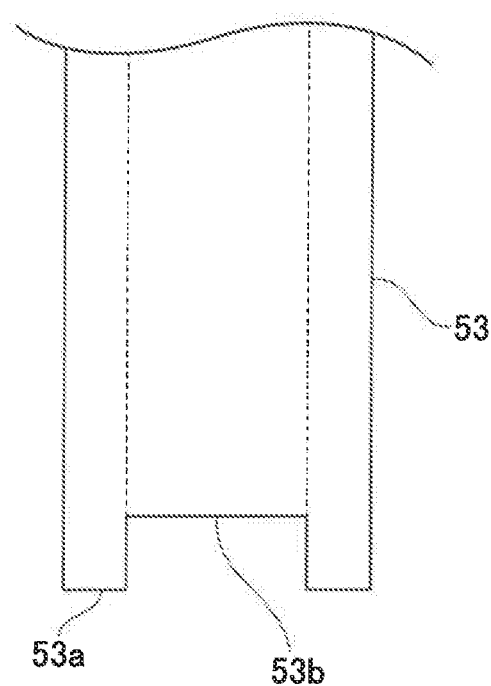
FIG. 20 shows a front end shape of a suction nozzle according to a third modification.

FIG. 20 shows a front end shape of a suction nozzle according to a third modification.

The suction nozzle 53 shown in FIG. 20 has an opening portion 53*a* having a planar shape that is perpendicular to an axial direction as in FIG. 17. However, slits 53*b* are formed in part of the opening portion 53*a*. It has a structure in which the width of the opening portion 53*a* and the inside diameter of the suction nozzle 53 (interval indicated by broken lines) are the same. For example, two slits 53*b* are formed in the circular opening portion 53*a* at an interval of 180 degrees. When a front end portion of the suction nozzle 53 is brought into contact with the bottom surface of the reactor vessel 3*a* or the bottom surface of the cleaning unit 24*a*, a gap is formed therebetween by the slits 53*b*. Therefore, suction force is not reduced. Consequently, the suction nozzle 53 according to the third modification provides the same effects as those provided by the first and second modifications. Further, when the front end portion of the suction nozzle 53 contacts the bottom surface of the reactor vessel 3*a* or the bottom surface of the cleaning unit 24*a*, the actual opening that can suck a liquid is smaller than those according to the first and second modifications. Although in the modification in FIG. 20, the width of the opening portion 53*a* is the same as the inside diameter of the suction nozzle 53, the width of the opening portion 53*a* may be smaller than the inside diameter of the suction nozzle 53.

Figure 21:
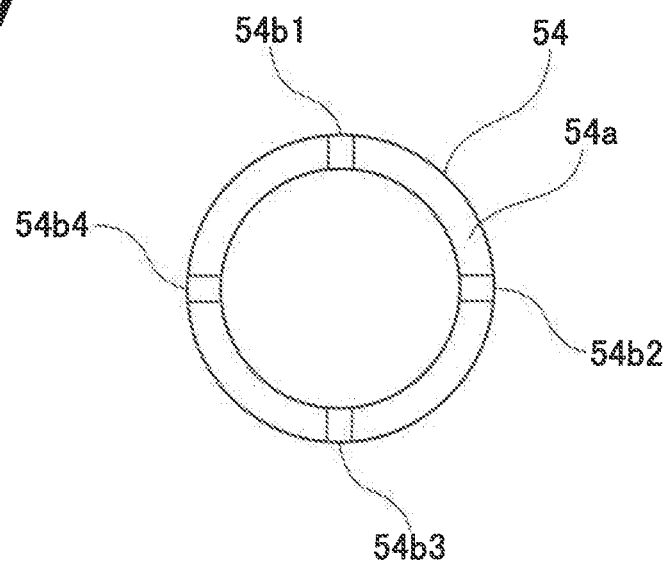
FIG. 21 shows a front end shape of a suction nozzle according to a fourth modification.

FIG. 21 shows a front end shape of a suction nozzle according to a fourth modification.

FIG. 21 is a plan view of the suction nozzle 54 according to a fourth modification as seen from therebelow. The suction nozzle 54 has an opening portion 54*a* having a planar shape that is perpendicular to an axial direction as in FIG. 17. However, for example, four slits 54*b*1 to 54*b*4 are formed in the circular opening portion 54*a* at an interval of 90 degrees. The suction nozzle 54 according to the fourth modification provides the same effects as those provided by the third modification. The slits 54*b*1 to 54*b*4 are formed at four locations in the suction nozzle 54, and, compared to the third modification in which the slits 53*b* are formed in two locations, a cleaning liquid amount that can be sucked per unit time is increased.

Although, in the first to third embodiments, the shape of the opening portion 22*a* at the front end of the discharge nozzle 22 has a planar shape that is perpendicular to the axial direction, the invention is not limited thereto.

Figure 22:
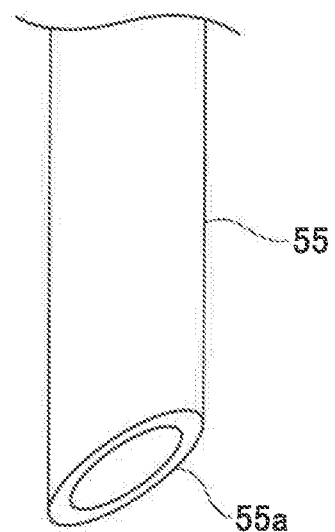
FIG. 22 shows an exemplary front end shape of a discharge nozzle.

FIG. 22 shows an exemplary front end shape of a discharge nozzle.

An opening portion 55a at the front end of the discharge nozzle 55 shown in FIG. 22 has a planar shape having a certain angle (such as 45 degrees) with respect to an axial direction. Here, the opening portion 55a is formed so as to oppose the suction nozzle (the suction nozzle is disposed on the right side of the discharge nozzle 55 in FIG. 22). When the opening portion 55a has a planar shape that is oblique to the axial direction in this way, an upper side of the oblique opening portion 55a contacts the suction nozzle. Therefore, a cleaning liquid discharged from the opening portion 55a flows along the suction nozzle more smoothly.

Although the embodiments according to the present invention are described above, the present invention is not limited to the above-described embodiments. Other modifications and applications are possible without departing from the gist of the present invention described in the claims.

For example, the above-described embodiments are used for specifically describing the structures of the devices and the systems in detail for making the description of the present invention easier to understand, and the present invention need not necessarily include all of the described structural features. In addition, part of the structural features of a certain embodiment may be replaced by other structural features, or the other structural features may be added to the structural features of a certain embodiment.

Although an example in which the automated analyzer 1 according to each of the above-described first to third embodiments is applied to an immunology test device performing the BF separating step is described, the nozzle cleaning technologies according to these embodiments are applicable to an automated analyzer including a nozzle that cleans reactor vessels of, for example, a biochemical analysis device.

The above-described first embodiment may be modified as follows.

For example, the first suction operation performed by the suction nozzle 23 need not be started before discharging a cleaning liquid. That is, the suction operation performed by the suction nozzle 23 may be performed after the high-concentration contaminated region of the suction nozzle 23 has been immersed in the cleaning liquid when the front end (opening portion 23a) of the suction nozzle 23 has reached the bottom surface of the cleaning unit 24a and a certain time has passed after the start of discharge of cleaning liquid. In this case, the cleaning liquid used in cleaning the low-concentration contaminated region of the suction nozzle 23 is contaminated due to contamination of a wall surface of the cleaning unit 24a. However, the number of discharges and suctions of the cleaning liquid (one discharge and two suctions in the first embodiment) are the same, so that control is easy to perform.

Although, in the above-described first embodiment, an example in which the discharge of cleaning liquid is started when the front end of the suction nozzle 23 (opening portion 23a) reaches the bottom surface of the cleaning unit 24a is described, the invention is not limited to this example. For example, the nozzle-21 downward movement starting process and the nozzle-21 downward movement ending process may be executed between a time immediately after the start of the nozzle cleaning operation and a time before starting the suction operation performed by the suction nozzle 23.

In the above-described third embodiment, in the case where a cleaning liquid is discharged after the nozzle 21 has been positioned to a height at which the front end of the suction nozzle 23 does not contact the bottom surface of the cleaning unit 24a, when the cleaning liquid is sucked by the suction nozzle 23, the nozzle 21 may be moved downward such that the front end (opening portion 23a) of the suction nozzle 23 follows the liquid surface of the cleaning liquid.

In order to adjust suction pressure, at a suction side, a trap that functions following the suction pressure and a pressurized tank that accommodates liquid recovered by the trap may be provided. When the suction pump 35 is used for purposes other than sucking a cleaning liquid, the suction electromagnetic valve 34 is not required.

REFERENCE SIGNS LIST 1 automated analyzer, 2 measuring device, 10 immune enzyme reaction unit, 11 first BF separating unit, 12 second BF separating unit, 21 nozzle, 22 discharge nozzle, 22a opening portion, 23 suction nozzle, 23a opening portion, 24 cleaning tank, 24a cleaning unit, 24b overflow unit, 24c discharge opening, 31 discharge electromagnetic valve, 32 discharge pump, 33 cleaning liquid tank, 34 suction electromagnetic valve, 35 suction pump, 40 controlling device, 41 control unit, 43 analyzing unit, W cleaning liquid

The invention claimed is:

1. An automated analyzer comprising:
a nozzle including a tubular discharge unit in fluid communication with a discharge pump and configured to discharge a cleaning liquid from an opening portion formed in a lower end thereof and a tubular suction unit in fluid communication with a suction pump and configured to suck the cleaning liquid discharged from the discharge unit through an opening portion formed in a lower end thereof, the discharge unit and the suction unit being disposed so as to contact in parallel in an axial direction, with the lower end of the discharge unit separated upwardly from the lower end of the suction unit, such that the cleaning liquid discharged from the opening portion of the discharge unit and running down an outer peripheral surface of the suction unit is sucked through the opening portion of the suction unit;
a cleaning tank fluidly connected at least to the discharge unit of the nozzle, in which the cleaning liquid that is discharged from the discharge unit accumulates; and
a control unit including a processor programmed to control an upward movement and a downward movement of the nozzle with respect to the cleaning tank, a discharge operation of the nozzle in which the cleaning liquid is discharged from the discharge unit, and a suction operation of the nozzle in which the suction unit sucks the cleaning liquid discharged from the discharge unit, the control unit connected to the discharge pump and the suction pump to control the discharge operation and the suction operation of the nozzle,
wherein the processor of the control unit is further programmed to cause, when cleaning the suction unit of the nozzle,
i) the downward movement of the nozzle to be started, and ended when the opening portion of the suction unit of the nozzle is positioned in the cleaning tank,
ii) the discharge operation f discharging the cleaning liquid by the discharge unit to be started,
iii) a first operation of the suction operation of suctioning the cleaning liquid by the suction unit to be started, and
iv) after causing the suction unit to suck the cleaning liquid running down the outer peripheral surface of the suction unit for a prescribed length of time, the first operation of the suction operation by the suction unit to end; next, v) after a prescribed amount of the cleaning liquid discharged from the opening portion of the discharge unit into the cleaning tank has accumulated after the first operation of the suction operation ended, the discharge operation by the discharge unit to end, and vi) a second operation of the suction operation by the suction unit to be started, with a predetermined portion of the suction unit, including the opening portion thereof, immersed in the cleaning liquid accumulated in the cleaning tank.

2. The automated analyzer according to claim 1, wherein the processor of the control unit is further programmed to cause the downward movement of the nozzle to be ended when the opening portion of the suction unit reaches a prescribed height from a bottom surface of the cleaning tank, and to cause the discharge operation by the discharge unit to be started after causing the downward movement of the nozzle to end.

3. The automated analyzer according to claim 2, wherein the processor of the control unit is further programmed to cause the downward movement of the nozzle to end when the opening portion of the suction unit reaches the bottom surface of the cleaning tank.

4. The automated analyzer according to claim 1, wherein the processor of the control unit is further programmed to cause the downward movement of the nozzle, the discharge operation by the discharge unit, and the first operation of the suction operation by the suction unit to be started at least partially temporally overlapped.

5. The automated analyzer according to claim 4, wherein the processor of the control unit is further programmed to cause, before causing the downward movement of the nozzle to end, the first operation of the suction operation by the suction unit to end, and, during the downward movement of the nozzle or after the opening portion of the suction unit has reached the bottom surface of the cleaning tank, the processor of the control unit causes the discharge operation by the discharge unit to end and the second operation of the suction operation by the suction unit to be started.

6. The automated analyzer according to claim 1, wherein the cleaning tank includes a cleaning unit into which the cleaning liquid discharged from the discharge unit is injected and accumulated therein, and an overflow unit into which the cleaning liquid that has overflowed from the cleaning unit flows, and wherein the processor of the control unit is further programmed to cause, when the cleaning liquid is accumulated in the cleaning unit of the cleaning tank such that a region having a prescribed height from the lower end of the suction unit is immersed therein, the second operation of the suction operation by the suction unit to be started.

7. The automated analyzer according to claim 1, wherein the processor of the control unit is further programmed to cause the discharge operation of the nozzle and the suction operation of the nozzle to have a relationship that a cleaning liquid amount per unit time that is sucked by the suction unit is greater than or equal to a cleaning liquid amount per unit time that is discharged by the discharge unit.

* * * * *

UNITED STATES PATENT AND TRADEMARK OFFICE
CERTIFICATE OF CORRECTION

PATENT NO. : 10,527,638 B2  
APPLICATION NO. : 15/310300  
DATED : January 7, 2020  
INVENTOR(S) : Nakamura Mizuki Page 1 of 1

It is certified that error appears in the above-identified patent and that said Letters Patent is hereby corrected as shown below:

In the Claims

Column 22, Line 61, Claim 1, delete "f" and insert -- of --

Signed and Sealed this  
Fifth Day of May, 2020

Andrei Iancu  
*Director of the United States Patent and Trademark Office*